United States Patent
Malafosse et al.

(10) Patent No.: US 11,723,956 B2
(45) Date of Patent: Aug. 15, 2023

(54) IMMUNOMODULATION AFTER LOCOREGIONAL ANTI-TUMORAL TREATMENT

(71) Applicants: Institut National de la Sante et de la Recherche Medicale (INSERM), Paris (FR); Centre National de la Recherche Scientifique (CNRS), Paris (FR); UNIVERSITÉ DE PARIS, Paris (FR); Assistance Publique—Hopitaux de Paris, Paris (FR); Ecole Nationale Superieure de Chimie de Paris, Paris (FR); Universite de Versailles—St Quentin en Yvelines, Versailles (FR)

(72) Inventors: Robert Malafosse, Paris (FR); Nathalie Mignet, Clamart (FR); Vincent Boudy, Paris (FR); Johanne Seguin, Kremlin Bicetre (FR); Kathia Lemdani, Paris (FR); Claude Capron, Boulogne (FR)

(73) Assignees: Institut National de la Sante et de la Recherche Medicale (INSERM), Paris (FR); Centre National de la Recherche Scientifique (CNRS), Paris (FR); Université de Paris, Paris (FR); Assistance Publique—Hopitaux de Paris, Paris (FR); Ecole Nationale Superieure de Chimie de Paris, Paris (FR); Universite de Versailles—St. Quentin en Yvelines, Versailles (FR)

( * ) Notice: Subject to any disclaimer, the term of this patent is extended or adjusted under 35 U.S.C. 154(b) by 0 days.

(21) Appl. No.: 16/327,543

(22) PCT Filed: Aug. 31, 2017

(86) PCT No.: PCT/EP2017/071924
§ 371 (c)(1),
(2) Date: Feb. 22, 2019

(87) PCT Pub. No.: WO2018/041981
PCT Pub. Date: Mar. 8, 2018

(65) Prior Publication Data
US 2019/0201492 A1    Jul. 4, 2019

(30) Foreign Application Priority Data

Aug. 31, 2016 (EP) ..................................... 16306102
May 16, 2017 (EP) ..................................... 17305558

(51) Int. Cl.
A61K 38/19   (2006.01)
A61K 39/07   (2006.01)
A61K 41/00   (2020.01)
A61K 47/10   (2017.01)
A61K 47/36   (2006.01)
A61P 35/00   (2006.01)
A61K 47/34   (2017.01)
A61K 9/00    (2006.01)
(Continued)

(52) U.S. Cl.
CPC .......... *A61K 38/193* (2013.01); *A61K 9/0019* (2013.01); *A61K 9/0024* (2013.01); *A61K 9/06* (2013.01); *A61K 31/765* (2013.01); *A61K 38/385* (2013.01); *A61K 39/04* (2013.01); *A61K 39/07* (2013.01); *A61K 39/39541* (2013.01); *A61K 41/0028* (2013.01); *A61K 41/0052* (2013.01); *A61K 47/10* (2013.01); *A61K 47/34* (2013.01); *A61K 47/36* (2013.01); *A61P 35/00* (2018.01); *C07K 16/2818* (2013.01); *A61K 2039/505* (2013.01); *A61K 2039/522* (2013.01); *A61K 2039/54* (2013.01); *A61K 2039/55522* (2013.01); *A61K 2039/585* (2013.01); *A61K 2039/82* (2018.08); *C07K 2317/76* (2013.01)

(58) Field of Classification Search
None
See application file for complete search history.

(56) References Cited

U.S. PATENT DOCUMENTS 5,124,151 A * 6/1992 Viegas ................. A61K 9/0019
                                                                   424/422
8,460,644 B2 * 6/2013 Meadows .............. A61K 31/54
                                                                   424/70.15
(Continued)

FOREIGN PATENT DOCUMENTS

WO    WO 02/102309      12/2002
WO    WO 2006014067   *  9/2006

OTHER PUBLICATIONS

Gregory Driessents et al. "Development of a successful antitumor therapeutic model combining in vivo dendritic cell vaccination with tumor irradiation and intratumoral GM-CSF delivery" 2011.*
(Continued)

*Primary Examiner* — Danah Al-Awadi
(74) *Attorney, Agent, or Firm* — Panitch Schwarze Belisario & Nadel LLP; Erin M. Dunston

(57) ABSTRACT

The present invention concerns a thermosensitive polymeric hydrogel comprising at least one thermosensitive copolymer, one aqueous solution, and a mucoadhesive excipient, wherein said thermosensitive polymeric hydrogel further comprises at least one immunostimulatory adjuvant and/or at least one cytokine and/or at least one chemokine and/or atleast one heat shockprotein. Another object of the invention is a thermosensitive polymeric hydrogel according to the invention for use in the treatment of tumors or metastasis in a subject having a cancer, preferably a metastatic cancer.

13 Claims, 13 Drawing Sheets

Figure 1:
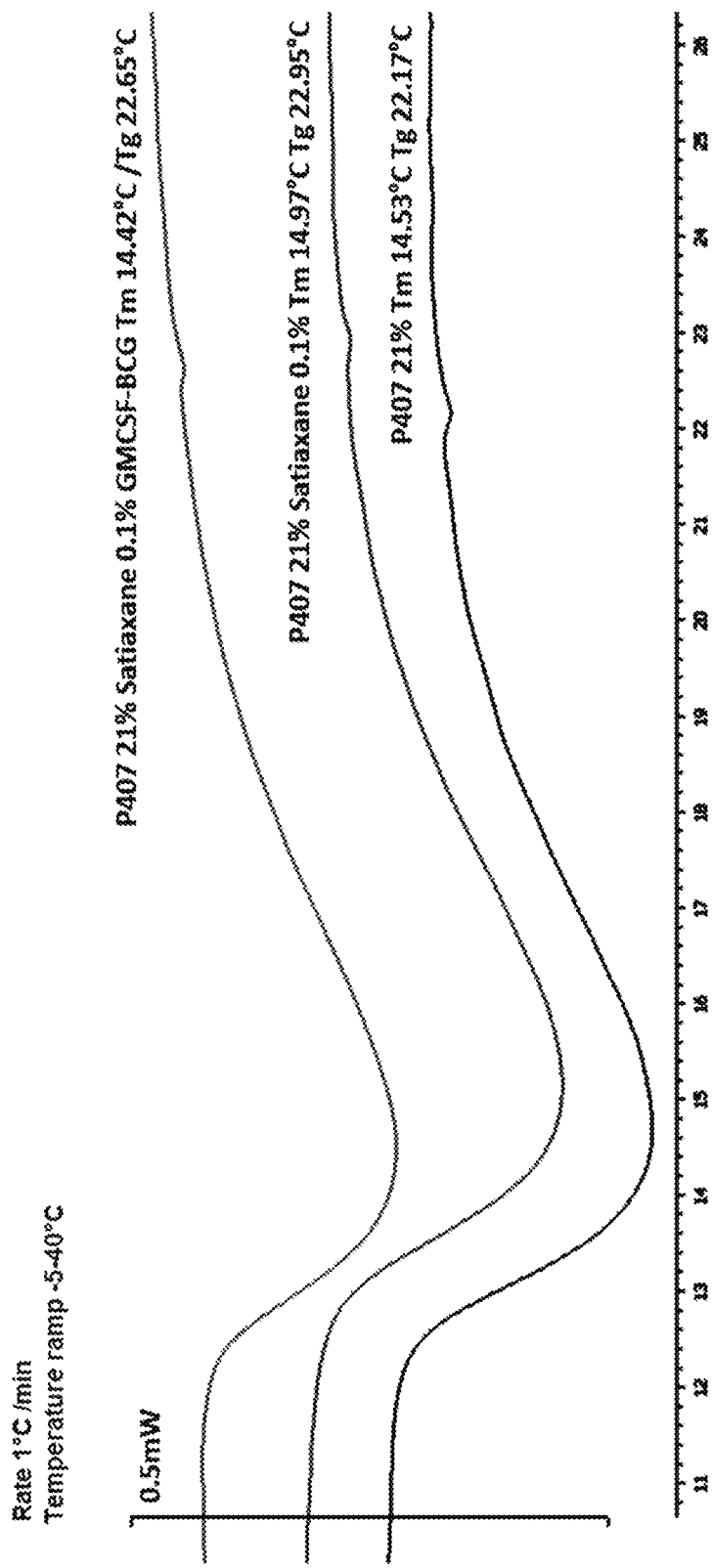

(51) Int. Cl.
  A61K 39/04    (2006.01)
  A61K 9/06     (2006.01)
  C07K 16/28    (2006.01)
  A61K 31/765   (2006.01)
  A61K 39/395   (2006.01)
  A61K 38/38    (2006.01)
  A61K 39/00    (2006.01)

(56) References Cited

U.S. PATENT DOCUMENTS

| | | | |
|---|---|---|---|
| 8,709,385 B2* | 4/2014 | Tamarkin | A61K 31/7056 424/78.05 |
| 2014/0105884 A1* | 4/2014 | Konorty | A61K 31/122 514/688 |
| 2014/0221307 A1* | 8/2014 | Gravett | A61P 17/02 514/54 |
| 2016/0271257 A1* | 9/2016 | Bredehorst | A61K 9/06 |

OTHER PUBLICATIONS

Driessens et al. "Development of a successful antitumor therapeutic model combining in vivo dendritic cell vaccination with tumor irradiation and intratumoral GM-CSF delivery" 2010.*
Darie "Rheological Investigation of Xanthan/Pluronic F127 hydrogels" 2014.*
Ma et al. "Novel Supramolecular hydrogel.micelle compsoite for co-delicery of anticancer drug and growth factor" 2012.*
Allard et al., *Linear quantification of lymphoid infiltration of the tumor margin: a reproducible method, developed with colorectal cancer tissues, for assessing a highly variable prognostic factor*, 7 Diagnostic Pathology 1-11 (2012).
Baggiolini, *Chemokines and leukocyte traffic*, 392 Nature 565-568 (Apr. 9, 1998).
Den Brok et al., *In Situ Tumor Ablation Creates an Antigen Source for the Generation of Antitumor Immunity*, 64 Cancer Research 4024-4029 (Jun. 1, 2004).
Driessens et al., *Development of a successful antitumor therapeutic model combining in vivo dendritic cell vaccination with tumor irradiation and intratumoral GM-CFS delivery*, 60 Cancer Immunol. Immunother. 273-281 (2011).
Govaert et al., *Does Radiofrequency Ablation Add to Chemotherapy for Unresectable Liver Metastases?*, 8 Curr. Colorectal Cancer Rep. 130-137 (2012).
Guo et al., [*Dendritic cell-cytokine induced killer cell immunotherapy combined with transcatheter arterialchemoembolization for hepatocellular carcinoma: safety and efficacy*]., 34(5) Nan Fang Yi Ke Da Xue Xue Bao 674-678 (May 2014) (abstract only).
Hänsler et al., *Activation and dramatically increased cytolytic activity of tumor specific T lymphocytes after radio-frequency ablation in patients with hepatocellular carcinoma and colorectal liver metastases*, 12(23) World J. Gatroenterol 3716-3721 (Jun. 21, 2006).
Hompes et al., *Radiofrequency ablation as a treatment tool for liver metastases of colorectal origin*, 11 Cancer Imaging 23-30 (2011).
Johnston et al., *Sustained Delivery of Interleukin-2 from a Poloxamer 407 Gel Matrix Following Intraperitoneal Injection in Mice*, 9(3) Pharmaceutical Research 425-434 (1992).
Liu et al., *Abrogation of Local Cancer Recurrence After Radiofrequency Ablation by Dendritic Cell-based Hyperthermic Tumor Vaccine*, 17(12) Molecular Therapy 2049-2057 (Dec. 2009).
Malfosse et al., *Surgical management of hepatic metastases from colorectal malignancies*, 12 Annals of Oncology 887-894 (2001).
Mosolits et al., *Towards therapeutic vaccines for colorectal carcinoma: a review of clinical trials*, 4(3) Future Drugs 329-350 (2005).
Nakamoto et al., *Combined therapy of transcatheter hepatic arterial embolization with intratumoral dendritic cell infusion for hepatocellular carcinoma: clinical safety*, 147 Clinical and Experimental Immunology 296-305 (2007).
Nemunaitis, *Vaccines in cancer: GVAX® a GM-CSF gene vaccine*, 4(3) Vaccine 259-274 (2005).
Nordlinger et al., *Perioperative FOLFOX4 chemotherapy and surgery versus surgery alone for resectable liver metastases from colorectal cancer (EORTC 70983): long-term results of a radomised, controlled, phase 3 trial*, 14 Lancet Oncology 1208-1215 (Nov. 2013).
Nordlinger et al., *Resection of liver metastases from colorectal cancer—how can we improve results?*, 5 Colorectal Disease 515-517 (2003).
Robinson et al., *Hematopoietic Progenitor Cell Mobilization in Mice by Sustained Delivery of Granulocyte Colony-Stimulating Factor*, 25 Journal of Interferon & Cytokine Research 490-500 (2005).
Rollins, *Chemokines*, 90(3) Blood 909-928 (Aug. 1, 1997).
Ruers et al., *Radiofrequency ablation combined with systemic treatment versus systemic treatment alone in patients with non-resectable colorectal live metastases: a randomized EORTC Intergroup phase II study (EORTC 40004)*, 23 Annals of Oncology 2619-2626 (2012).
Su et al., *The Efficacy and Safety of Dendritic Cells Co-Cultured with Cytokine-Induced Killer Cell Therapy in Combination with TACE-Predominant Minimal-Invasive Treatment for Hepatocellular Carcinoma: a Meta-Analysis*, 62 Clin. Lab 1-10 (Apr. 2016).
Zhang et al., *A magnetic chitosan hydrogel for sustained and prolonged delivery of Bacillus Calmette-Guérin in the treatment of bladder cancer*, 34 Biomaterials 10258-10266 (2013).

* cited by examiner

B

A

B

A

B

A

B

A

B

C

D

IMMUNOMODULATION AFTER LOCOREGIONAL ANTI-TUMORAL TREATMENT

CROSS-REFERENCE TO RELATED APPLICATIONS

This application is a U.S. National Stage Application pursuant to 35 U.S.C. § 371 of International Patent Application PCT/EP2017/071924, filed on Aug. 31, 2017, and published as WO 2018/041981 on Mar. 8, 2018, which claims priority to European Patent Application 17305558.3, filed on May 16, 2017, and European Patent Application 16306102.1, filed on Aug. 31, 2016, all of which are incorporated herein by reference in their entireties for all purposes.

The present invention is directed to a thermosensitive polymeric hydrogel comprising at least one thermosensitive copolymer, one aqueous solution, a mucoadhesive excipient, wherein said thermosensitive polymeric hydrogel further comprises at least one immunostimulatory adjuvant and/or at least one cytokine and/or at least one chemokine and/or at least one heat shock protein. Another object of the invention is a thermosensitive polymeric hydrogel according to the invention for use in the treatment of tumors or metastasis in a subject having a cancer, preferably a metastatic cancer.

Colorectal cancer (CRC) is the third most common cancer in the world, with liver metastases occurring in approximately 50% of cases. Surgical treatment with curative intent is not possible in 70% of patients. Chemotherapies and targeted biological therapies have limited efficacy because of toxicity and development of resistance to treatment. Locoregional treatments such as localized thermal treatments or regional intra-arterial chemoembolization are used to treat primary and metastatic liver tumors when resection is not feasible. In particular, it has been shown that radiofrequency ablation (RFA), which is widely used for the treatment of non resectable liver metastases, induces an immune response, but is insufficient to prevent recurrence. However, half of the patients who have had a complete treatment develop intrahepatic recurrence and/or progression of occult micrometastases. An anti-tumor immune response was clearly demonstrated in those patients treated with localized heat treatments (den Brok et al., 2004; Hansler et al., 2006) or regional chemoembolization (Guo et al., 2014; Su et al., 2016). However, colorectal cancer has only a low effect on the immune system leading to high rates of local and systemic recurrence after 3 years which compromise these results (Ruers et al., 2012 and Nordlinger et al., 2013).

There is therefore a need of a new product and method to enhance the immune system response toward colorectal cancer to prevent recurrence and/or growth of occult micrometastases in subjects suffering from cancer or metastatic cancer, thereby increasing the survival rate after 3 years.

The object of the invention is a thermosensitive hydrogel comprising one or more immunostimulatory species, such as molecule or protein, in combination with a locoregional treatment of tumor or metastases. This strategy enhances the anti-tumor immune response lasting for a remotely controlled metastatic disease. Potentiation of thermal or ischemic cell stress by immunomodulator(s) vectorized in situ by the hydrogel, targets two fundamental concepts of the anti-tumoral immune response, recruitment and maturation of antigen presenting cells (APCs).

Accordingly, the present invention relates to a thermosensitive polymeric hydrogel comprising:

- at least one thermosensitive copolymer selected from poloxamers; PEG-PLGA-PEG copolymers; PEG-PLA-PEG copolymers; PEG-PCL-PEG copolymers; preferably poloxamers, and more preferably is poloxamer 407 and/or poloxamer 188;
- at least one aqueous solution at a concentration between 67% w/v and 83% w/v, preferentially between 75% w/v and 83% w/v, more preferentially between 77% w/v and 82% w/v;
- a mucoadhesive excipient, at a concentration between 0 and 0.3% w/v, preferentially between 0.01% w/v and 0.3% w/v, more preferentially between 0.01% w/v and 0.2% w/v, selected from carraghenan, xanthan gum, gellan gum, sodium alginate, chitosan, and dextran;
- wherein said thermosensitive polymeric hydrogel further comprises at least one immunostimulatory adjuvant and/or at least one cytokine and/or at least one chemokine and/or at least one heat shock protein.

In a preferred embodiment, the thermosensitive polymeric hydrogel according to the invention comprises at least two copolymers, preferably selected from poloxamers, such as poloxamers 407 and 188.

The term "thermosensitive copolymer" can be defined as a copolymer having phase change behavior in response to a change in temperature. The thermosensitive copolymer used herein undergoes a solution-to-gel (sol-gel) transition, or gelation, in a certain solvent (e.g. water) in response to an increase in temperature above a certain threshold, described herein as the transition temperature. At a temperature lower than the transition temperature, the copolymer may be easily dissolved to form a solution (e.g. an aqueous solution). At a temperature higher than or equal to the transition temperature, the solubility of the copolymer may sharply decrease to form aggregated particles, resulting from, for example, the association of polymer molecules and water expulsion. The transition temperature at or above which a solution of a thermosensitive copolymer undergoes partial phase change to form a gel may exist in a range of about 10° C. to about 50° C., for example about 25° C. to about 50° C., and specifically about 28° C. to 35° C. The sol-gel transition of the thermosensitive copolymer used herein is preferentially reversible, and is dependent on the composition of the solution and/or gel.

The thermosensitive copolymers suitable for the present invention are selected from:

- pluronic polymers (also designated as "poloxamers") which are copolymers based on ethylene oxide and propylene oxide;
- PEG-PLGA-PEG copolymers (with "PEG" for "polyethyleneglycol" and "PLGA" for "poly(co-glycolic acid)");
- PEG-PLA-PEG copolymers (with "PLA" for "poly(lactic acid)");
- PEG-PCL-PEG copolymers (with "PCL" for "polycaprolactone");
- preferably poloxamers, said thermosensitive copolymer being more preferably poloxamer 407 (or P407).

In a preferred embodiment, the thermosensitive polymeric hydrogel according to the invention comprises poloxamer 407 and/or poloxamer 188 in a concentration between 17% w/v and 32% w/v, preferably between 17% w/v and 28% w/v, more preferably 17% w/v and 24% w/v, even more preferably between 18% w/v and 22% w/v.

In a preferred embodiment, the thermosensitive polymeric hydrogel according to the invention comprises one poloxamer, preferably P407, or a combination of poloxamers, such as P407 and P188, in a concentration between 17% w/v and 32% w/v, preferably between 17% w/v and 28% w/v, more preferably 17% w/v and 24% w/v, even more preferably between 18% w/v and 22% w/v. For example, the copolymer according to the invention comprises P407 preferably at a concentration between 17% w/v and 32% w/v, preferably between 17% w/v and 28% w/v, more preferably 17% w/v and 24% w/v, even more preferably between 18% w/v and 22% w/v.

The term "aqueous solution" is defined herein as liquid compositions such as filtered water, sodium chloride, phosphate buffered saline (PBS), sodium acetate, sodium citrate, glucose, lactose, and/or trehalose, and the like. P407, when solubilized in aqueous solution has good solubilizing capacity, low toxicity and shows thermoreversible properties.

Typically, the thermogel composition of the invention comprises more than 60% w/v of water, even more preferably more than 65% w/v water, even more preferably between 67% w/v and 83% w/v of water, more preferably between 75% w/v and 81% w/v of water, more preferentially between 77% w/v and 79% w/v of water. Said water is preferably sterile water (such as ultrapure water or water for injection).

Such "aqueous" compositions are typically homogeneous.

By "mucoadhesive excipient" it is meant herein a product allowing the composition to be administered as a flowable liquid but that reinforce gel cohesion upon gelation and gel interactions with the tissue of interest, thereby providing a bioadhesive effect which acts to hold the therapeutic agents at the site of interest for an extended period of time. Mucoadhesive polymer excipients, such as carraghenan, xanthan gum (e.g. Satiaxane®), gellan gum, sodium alginate (e.g. Protanal), chitosan, and dextran are examples of materials which when formulated into a suitable composition will gelify on the tissue of interest. The composition according to the invention containing xanthan gum (e.g. Satiaxane®) or gellan gum will typically consist of a concentration between 0.01% w/v and 0.3% w/v, preferably between 0.05% w/v and 0.2% w/v, more preferably between 0.1% w/v and 0.2% w/v of the xanthan or gellan gum.

By "stress protein" also called "heat shock protein" or "HSP" it is meant herein a family of proteins that are produced by cells in response to exposure to stressful conditions. Such stressful conditions are (but not limited) cold, heat, UV light. HSP useful in the context of the invention are for example GP96 and HSP70.

In a preferred embodiment, the thermosensitive polymeric hydrogel according to the invention allows controlling release of said immunostimulatory adjuvant and/or said cytokine and/or said chemokine and/or said heat shock protein, under physiological conditions, over a period from at least 12 hours to 12 days, preferably at least 24 hours to 10 days, more preferably at least 3 to 7 days, even more preferably 7 days.

According to the present invention, the term "adjuvant" means a compound that is administered for the purpose of enhancing immunogenicity of an antigen or a vaccine, and in the present specification, it is expressed as "immunostimulatory adjuvants" or merely "adjuvant". Herein "immunostimulatory adjuvant" are administered to an animal to stimulate an immune response against an antigen which can be derived from bacterial cells, mycobacterial cells, or virus wherein said bacterial cells can be killed, live and/or attenuated, for example, BCG, which is a live attenuated bacterial vaccine. Bacterial vaccines can either be a live bacterial vaccine, a killed bacterial vaccine, an attenuated bacterial vaccine, or purified proteins such as a purified protein derivatives (PPDs) from BCG or a fragment of bacterial DNA such as CpG oligodeoxynucleotides (or CpG ODN), as known in the art or can be produced by methods well known to a person of ordinary skill in the art using routine experimentation.

The adjuvant of the present invention may be used alone, or two or more may be used in combination. In particular, if there is a synergy effect among the adjuvants, it is preferable that two or more adjuvants exerting the synergy effect are used in combination. In other cases, an adjuvant may be used alone, but in accordance with the purpose, the adjuvant may be used in combination.

As used herein, the term "antigen" means any biological molecule (proteins, peptides, nucleotides/oligodeoxynucleotides, lipoproteins, glycans, glycoproteins) that is capable of eliciting an immune response against itself or portions thereof, including but not limited to, tumor associated antigens and viral, bacterial, parasitic, and fungal antigens.

In a preferred embodiment, the thermosensitive polymeric hydrogel according to the invention comprises at least one immunostimulatory adjuvant selected from:
  i. BCG and/or at least one of its purified proteins (in particular PPDs), or
  ii. a fragment of bacterial DNA such as CpG oligodeoxynucleotides (or CpG ODN), attenuated bacterial and viral agents and derivatives thereof, such as *Listeria monocytogenes, Salmonella typhimurium*, and HPV16 E7 (rE7m) protein. Advantageously, said anti-tumoral activity is a specific or a non-specific anti-tumoral activity, or
  iii. heat killed bacteria selected from: *Mycobacterium tuberculosis* (HKMT), *Salmonella typhimurium* (HKST), *Listeria monocytogenes* (HKLM), *Mycobacterium vaccae*, IMM-101 (*Mycobacterium obuense*) and inactivated *Streptococcus pyogenes* (OK-432/Picibanil) and their combination thereof; or
  iv. a Lps analogue selected from: MPLA (monophosphoryl lipid A), G100 (glucopranosyl lipid A) and their combination thereof; or
  v. a synthetic analogue selected from: Imiquimod, mifamurtide (Synthetic wall analogue of *Mycobacterium tuberculosis*) and their combination thereof.

In a preferred embodiment, the thermosensitive polymeric hydrogel according to the invention comprises at least one immunostimulatory adjuvant selected from:
  BCG and/or at least one of its purified proteins (in particular PPDs), or
  a fragment of bacterial DNA such as CpG oligodeoxynucleotides (or CpG ODN), attenuated bacterial and viral agents and derivatives thereof, such as *Listeria monocytogenes, Salmonella typhimurium*, and HPV16 E7 (rE7m) protein. Advantageously, said anti-tumoral activity is a specific or a non-specific anti-tumoral activity.

By "non-specific anti-tumoral activity" it is meant herein that said agent is not immunogenic itself, but is capable of stimulating various non-specific effector mechanisms of the immune system against cancer tumor. On the contrary, "specific anti-tumoral activity" refers to an agent capable of stimulating various specific effector mechanisms of the immune system against cancer tumor. The term "anti-tumoral" refers to a compound or composition that can inhibit or prevent cancer growth, invasion, and/or metastasis.

The term "cytokine" as used herein refers to the general class of biological molecules which effect/affect cells of the immune system. The definition is meant to include, but is not limited to, those biological molecules that act locally or may circulate in the blood, and which, when used in the compositions or methods of the present invention serve to regulate or modulate an individual's immune response to cancer. Exemplary cytokines for use in practicing the invention include but are not limited to interferon-alpha (IFN-α), interferon-beta (IFN-ß), and interferon-gamma (IFN-γ), interleukins (e.g. among IL-1 to IL-29, in particular, IL-2, IL-5, IL-6, IL-7, IL-12, IL-15 and IL-18), tumor necrosis factors (e.g., TNF-alpha and TNF-beta), erythropoietin (EPO), intracellular adhesion molecule (ICAM), macrophage colony stimulating factor (M-CSF), granulocyte colony stimulating factor (GCSF) and granulocyte-macrophage colony stimulating factor (GM-CSF).

As used herein, the term "chemokine" refers to a member of a group of art-recognized proteins that act as chemo attractants for host defense effector cells such as neutrophils, monocytes and lymphocytes (see, for example, Rollins, 1997 and Baggiolini, 1998). Preferred chemokines are members of the "CC" and "CXC" chemokine classes, and include: CCL21-CCL19-CCR7; CCL2 (or monocyte chemotactic protein [MCP-1]), CCL3, CCL5, CCL16 (liver-expressed chemokine [LEC]), CXCL12-CXCR7, CCL20 (or MIP3a), and other chemokines with chemotactic activity for monocytes, dendritic cells such as MDC (STCP 1). More preferred are CCL2, CCL19, and CCL21. Most preferred is CCL21.

The term "stress protein" as used herein, is understood to mean any cellular protein which satisfies one or more, preferably all the following criteria. It is a protein whose intracellular concentration increases when a cell is exposed to stressful stimuli, is capable of binding other proteins or peptides, and is capable of releasing the bound proteins or peptides in the presence of adenosine triphosphate (ATP) and/or low pH. Stressful stimuli include, but are not limited to, heat shock, nutrient deprivation, metabolic disruption, oxygen radicals, and infection with intracellular pathogens.

The first stress proteins to be identified were the heat shock proteins (HSP's). As their name suggests, HSP's typically are induced by a cell in response to heat shock. Three major families of mammalian HSP's have been identified to date and include HSP60, HSP70 and HSP90. The numbers reflect the approximate molecular weight of the stress proteins in kilodaltons. Members of the mammalian HSP 90 family identified to date include cytosolic HSP90 (also known as Hsp83) and the endoplasmic reticulum counterparts HSP90 (also known as HSP83), HSP87, Grp94 (also known as ERp99) and gp96. Members of the HSP70 family identified to date include: cytosolic HSP70 (also known as p73) and Hsc70 (also known as p72); the endoplasmic reticulum counterpart BiP (also known as Grp78); and the mitochondrial counterpart HSP 70 (also known as Grp75).

In a preferred embodiment, the thermosensitive polymeric hydrogel according to the invention comprises at least one cytokine and/or one chemokine and/or one heat shock protein selected from GMCSF, GCSF, IL-12, Interferon γ, TNF α, GP96, HSP, HSP70, preferably GMCSF.

Another object of the present invention is a thermosensitive polymeric hydrogel for use as a medicament comprising:
  at least one thermosensitive copolymers described above;
  at least one aqueous solution at a concentration between 67% w/v and 83% w/v, preferentially between 75% w/v and 83% w/v, preferentially between 77% w/v and 82% w/v;
  a mucoadhesive excipient at a concentration between 0 and 0.3% w/v, preferentially between 0.01% w/v and 0.3% w/v, more preferentially between 0.01% w/v and 0.2% w/v, selected from carraghenan, xanthan gum, gellan gum, sodium alginate, chitosan, and dextran;
  wherein said thermosensitive polymeric hydrogel further comprises at least one immunostimulatory adjuvant and/or at least one cytokine and/or at least one chemokine and/or at least one heat shock protein.

In a preferred embodiment, the thermosensitive polymeric hydrogel for use as a medicament according to the invention comprises at least two copolymers, preferably selected from poloxamers, such as poloxamers 407 and 188.

The thermosensitive polymeric hydrogel for use as a medicament according to the invention comprises at least one thermosensitive copolymer selected from:
  poloxamers;
  PEG-PLGA-PEG copolymers;
  PEG-PLA-PEG copolymers;
  PEG-PCL-PEG copolymers;
  preferably poloxamers, more preferably are poloxamers 407 and/or 188.

Advantageously, the thermosensitive polymeric hydrogel for use as a medicament according to the invention comprises poloxamer 407 and/or 188 at a concentration between 17% w/v and 32% w/v, preferably between 17% w/v and 28% w/v, more preferably 17% w/v and 24% w/v, even more preferably between 18% w/v and 22% w/v, or a combination of poloxamers, such as poloxamer 407 and poloxamer 188.

In a preferred embodiment, thermosensitive polymeric hydrogel for use as a medicament according to the invention has an osmolarity comprised between 200 and 600 mOsm, preferentially between 300 and 500 mOsm, preferentially between 350 and 450 mOsm.

Determination of "osmolarity" is easily made by routine experimentation procedures which are known by the person skilled in the art.

In a preferred embodiment, the thermosensitive polymeric hydrogel for use as a medicament according to the invention allows controlling the release of said immunostimulatory adjuvant and/or said cytokine and/or said chemokine and/or said heat shock protein, under physiological conditions, over a period from at least 12 hours to 12 days, preferably at least 24 hours to 10 days, more preferably at least 3 to 7 days, even more preferably 7 days.

In a preferred embodiment, the thermosensitive polymeric hydrogel for use as a medicament according to the invention comprises at least one immunostimulatory adjuvant selected from BCG and/or at least one of its purified proteins such as PPDs, or a fragment of bacterial DNA such as CpG oligodeoxynucleotides (or CpG ODN), attenuated bacterial or viral agents and derivatives thereof having a specific or a non-specific anti-tumoral activity, such as *Listeria monocytogenes, Salmonella typhimurium*, and HPV16 E7 (rE7m) protein.

In a preferred embodiment, the thermosensitive polymeric hydrogel for use as a medicament according to the invention comprises at least one cytokine and/or chemokine and/or heat shock protein selected from GMCSF, GCSF, IL-12, Interferon γ, TNF α, GP96, HSP, HSP70, preferably GMCSF.

Another object of the present invention is a thermosensitive polymeric hydrogel for use in the treatment of tumors or metastasis in a subject having a cancer, said hydrogel comprising:
  at least one thermosensitive copolymer as described above;

at least one aqueous solution at a concentration between 67% w/v and 83% w/v, preferentially between 75% w/v and 83% w/v, more preferentially between 77% w/v and 82% w/v;

a mucoadhesive excipient at a concentration between 0 and 0.3% w/v, preferentially between 0.01% w/v and 0.3% w/v, more preferentially between 0.01% w/v and 0.2% w/v, selected from carraghenan, xanthan gum, gellan gum, sodium alginate, chitosan, and dextran;

wherein said thermosensitive polymeric hydrogel further comprises at least one immunostimulatory adjuvant and/or at least one cytokine and/or at least one chemokine and/or at least one heat shock protein.

In a preferred embodiment, the thermosensitive polymeric hydrogel for use in the treatment of tumors or metastasis in a subject having a cancer according to the invention comprises at least two copolymers, preferably selected from poloxamers, such as poloxamers 407 and 188.

The term "tumor" is defined as one or more tumor cells capable of forming an invasive mass that can progressively displace or destroy normal tissues.

The term "metastasis" refers to the spread of malignant tumor cells from one organ or part to another non-adjacent organ or part. Cancer cells can "break away", "leak", or "spill" from a primary tumor, enter lymphatic and blood vessels, circulate through the bloodstream, and settle down to grow within normal tissues elsewhere in the body. When tumor cells metastasize, the new tumor is called a secondary or metastatic cancer or tumor. The term "micrometastasis" refers to metastasis not detectable upon treatment and development thereof after treatment is responsible for recurrence. The term "macrometastasis" refers to metastasis which are visible at the time of treatment; they are treated or left in place (other part of the liver, lung, . . . ).

In a preferred embodiment, the thermosensitive polymeric hydrogel for use in the treatment of cancer tumors or metastasis according to the invention comprises at least one thermosensitive copolymer selected from:

poloxamers;
PEG-PLGA-PEG copolymers;
PEG-PLA-PEG copolymers;
PEG-PCL-PEG copolymers;
preferably poloxamers, said thermosensitive copolymer being more preferably poloxamers 407 and/or 188.

In a preferred embodiment, the thermosensitive polymeric hydrogel for use in the treatment of cancer tumors or metastasis according to the invention comprises poloxamer 407 and/or poloxamer 188 in a concentration between 17% w/v and 32% w/v, preferably between 17% w/v and 28% w/v, more preferably 17% w/v and 24% w/v, even more preferably between 18% w/v and 22% w/v.

In a particular embodiment, the thermosensitive polymeric hydrogels for use in the treatment of cancer tumors or metastasis according to the invention present an osmolarity comprised between 200 and 600 mOsm, between 300 and 500 mOsm, preferentially between 350 and 450.

In a preferred embodiment, the thermosensitive polymeric hydrogels for use in the treatment of cancer tumors or metastasis according to the invention allow to control release of said immunostimulatory adjuvant and/or said cytokine and/or said chemokine and/or said heat shock protein, under physiological conditions, over a period from at least 12 hours to 12 days, preferably at least 24 hours to 10 days, more preferably at least 3 to 7 days, even more preferably 7 days.

In a preferred embodiment, the thermosensitive polymeric hydrogels are for use in the treatment of cancer tumors or metastasis selected from colorectal cancer, hepatocellular carcinoma, melanoma, kidney cancer, lung cancer, breast cancer, pancreatic cancer and bone cancer, preferably a metastatic cancer thereof, more preferably metastasis of a colorectal cancer.

In a preferred embodiment, the thermosensitive polymeric hydrogel for use in the treatment of cancer tumors or metastasis according to the invention comprises at least one immunostimulatory adjuvant selected from BCG and/or from at least one of its purified proteins such as PPDs, or a fragment of bacterial DNA such as CpG oligodeoxynucleotides (or CpG ODN), or any attenuated bacterial or viral agents and derivatives thereof having a specific or a non-specific anti-tumoral activity, such as *Listeria monocytogenes, Salmonella typhimurium*, and HPV16 E7 (rE7m) protein.

In a preferred embodiment, the thermosensitive polymeric hydrogels for use in the treatment of cancer tumors or metastasis according to the invention comprises at least one cytokine and/or chemokine and/or heat shock protein selected from GMCSF, GCSF, IL 12, Interferon γ, TNF α, GP96, HSP, HSP70, preferably GMCSF.

In a preferred embodiment, the thermosensitive polymeric hydrogel for use in the treatment of cancer tumors or metastasis according to the invention is used along with a locoregional treatment, such as radiofrequency, microwaves, cryotherapy, or embolization, preferentially radiofrequency, and/or an anti-tumoral treatment, such as radiotherapy, targeted chemotherapy, biotherapy, or systemic immunotherapy. Preferentially, the thermosensitive polymeric hydrogel for use in the treatment is administered concomitantly or sequentially, preferentially concomitantly with a locoregional treatment and sequentially with an anti-tumoral treatment.

The term "administered concomitantly" means administering the agents and/or locoregional treatment substantially concurrently. The term "administered concomitantly" encompasses not only administering the different locoregional treatment and/or agents in a single pharmaceutical dosage form but also the administration of each locoregional treatment and/or active agent in its own separate pharmaceutical dosage. Where separate locoregional treatment and/or dosage formulations are used, they can be administered at essentially the same time, i.e., concurrently.

The term "sequentially administering" means administering the locoregional treatment and/or agents at separately staggered times.

In a preferred embodiment, the thermosensitive polymeric hydrogel for use in the treatment of cancer tumors or metastasis is used as described above, with a systemic immunotherapy which is a systemic immune checkpoint inhibitor or a systemic immune checkpoint blockade.

The term "systemic immune checkpoint" means immune checkpoint which prevents the activation of circulating lymphocytes, inhibiting as a consequence the immune response. The term "immune checkpoint" means a signal for regulating the antigen recognition of T cell receptor (TCR) in the process of immune response. The term "immune checkpoint inhibitors" refers to molecules or receptor-ligand interactions coaching stimulation or inhibition of the immune response, which can be used for treatments helping the body to recognize and to attack cancer cells or metastasis.

The term "systemic immune checkpoint blocade" means the use of a molecule or a biomolecule which block the effect of the systemic immune checkpoint to restore the immune response.

In a preferred embodiment, the systemic immune check point inhibitor is selected from: anti-PD1, anti-CTLA4, anti-PDL1, anti-TIM3, anti-LAG3, anti-IDO, anti-Kir, anti-blta and their combination thereof.

In a preferred embodiment, the thermosensitive polymeric hydrogel for use in the treatment of cancer tumors or metastasis according to the invention is used with a locoregional treatment, such as RFA, and an antitumoral treatment, such as systemic immunotherapy.

Preferentially, the thermosensitive polymeric hydrogel for use in the treatment of cancer tumors or metastasis is administered concomitantly or sequentially, preferentially concomitantly with a RFA and sequentially with a systemic immune check point inhibitor that is selected from: anti-PD1, anti-CTLA4, anti-PDL1, anti-TIM3, anti-LAG3, anti-IDO, anti-Kir, anti-blta and their combination thereof.

Another object of the present invention is a kit comprising:
i. a thermosensitive polymeric hydrogel comprising:
   at least one thermosensitive copolymer as described above;
   at least one aqueous solution according to the invention at a concentration between 67% w/v and 83% w/v, preferentially between 75% w/v and 83% w/v, more preferentially between 77% w/v and 82% w/v;
   a mucoadhesive excipient according to the invention at a concentration between 0 and 0.3% w/v, preferentially between 0.01% w/v and 0.3% w/v, more preferentially between 0.01% w/v and 0.2% w/v, selected from carraghenan, xanthan gum, gellan gum, sodium alginate, chitosan, and dextran;
ii. at least one immunostimulatory adjuvant selected from:
   BCG and/or at least one of its purified proteins such as PPDs, or
   a fragment of bacterial DNA such as CpG oligodeoxynucleotides (CpG ODN),
   attenuated bacterial and viral agents and derivatives thereof having a specific, or
   a non-specific anti-tumoral activity, such as *Listeria monocytogenes, Salmonella typhimurium*, and HPV16 E7 (rE7m) protein, or
   heat killed bacteria selected from: *Mycobacterium tuberculosis* (HKMT), *Salmonella typhimurium* (HKST), *Listeria monocytogenes* (HKLM), *Mycobacterium vaccae*, IMM-101 (*Mycobacterium obuense*) and inactivated *Streptococcus pyogenes* (OK-432/Picibanil) and their combination thereof; or
   Lps analogue selected from: MPLA (monophosphoryl lipid A), G100 (glucopranosyl lipid A) and their combination thereof; or
   synthetic analogue selected from: Imiquimod, mifamurtide (Synthetic wall analogue of *Mycobacterium tuberculosis*) and their combination thereof;
iii. at least one cytokine and/or at least one chemokine and/or at least one heat shock protein selected from GMCSF, GCSF, IL12, Interferon γ, TNF α, GP96, HSP, HSP70, preferably GMCSF;
iv. optionally a notice of use.

Advantageously, the kit according to the invention comprises:
i. a thermosensitive polymeric hydrogel comprising:
   at least one thermosensitive copolymer as described above;
   at least one aqueous solution according to the invention at a concentration between 67% w/v and 83% w/v, preferentially between 75% w/v and 83% w/v, more preferentially between 77% w/v and 82% w/v;
   a mucoadhesive excipient according to the invention at a concentration between 0 and 0.3% w/v, preferentially between 0.01% w/v and 0.3% w/v, more preferentially between 0.01% w/v and 0.2% w/v, selected from carraghenan, xanthan gum, gellan gum, sodium alginate, chitosan, and dextran;
ii. at least one immunostimulatory adjuvant selected from BCG and/or at least one of its purified proteins such as PPDs, or a fragment of bacterial DNA such as CpG oligodeoxynucleotides (CpG ODN), attenuated bacterial and viral agents and derivatives thereof having a specific or a non-specific anti-tumoral activity, such as *Listeria monocytogenes, Salmonella typhimurium*, and HPV16 E7 (rE7m) protein;
iii. at least one cytokine and/or at least one chemokine and/or at least one heat shock protein selected from GMCSF, GCSF, IL12, Interferon γ, TNF α, GP96, HSP, HSP70, preferably GMCSF;
iv. optionally a notice of use.

In a preferred embodiment, the kit according to the invention comprises at least two copolymers, preferably selected from poloxamers, such as poloxamers 407 and 188.

In a preferred embodiment, the kit according to the invention comprises a thermosensitive copolymer selected from:
poloxamers;
PEG-PLGA-PEG copolymers;
PEG-PLA-PEG copolymers;
PEG-PCL-PEG copolymers;
preferably poloxamers, said thermosensitive copolymer being more preferably poloxamer 407 and/or poloxamer 188.

Advantageously, said poloxamers 407 and/or 188 are at a concentration between 17% w/v and 32% w/v, preferably between 17% w/v and 28% w/v, more preferably 17% w/v and 24% w/v, even more preferably between 18% w/v and 22% w/v.

Another object of the present invention is a method of treatment of a subject having a cancer comprising at least the following steps:
administering a locoregional treatment, such as radiofrequency, microwaves, cryotherapy, or arterial embolization, preferentially radiofrequency, or an anti-tumoral treatment; and
injecting in at least one said cancer tumor or metastasis said thermosensitive polymeric hydrogel according to the invention; and
stimulating immune system in said subject by administering an immunostimulatory adjuvant selected from BCG and/or at least one of its purified proteins, or CpG oligodeoxynucleotides (or CpG ODN), attenuated or derived from bacterial and viral agents and derivatives thereof, such as *Listeria monocytogenes, Salmonella typhimurium*, and HPV16 E7 (rE7m) protein; and/or
administering a cytokine and/or a chemokine and/or a heat shock protein according to the invention.

Another object of the invention is a method of treatment of a subject having a cancer comprising at least the following steps:
administering a locoregional treatment, such as radiofrequency, microwaves, cryotherapy, or arterial embolization, preferentially radiofrequency, or an anti-tumoral treatment; and
injecting into at least one said cancer tumor or metastasis said thermosensitive polymeric hydrogel according to the invention; and stimulating immune system in said subject by administering an immunostimulatory adjuvant selected from BCG and/or at least one of its purified proteins, or CpG oligodeoxynucleotides (or CpG ODN), attenuated or derived from bacterial and viral agents and derivatives thereof, such as *Listeria monocytogenes, Salmonella typhimurium*, and HPV16 E7 (rE7m) protein; and/or administering a cytokine and/or a chemokine and/or a heat shock protein according to the invention; and administering a systemic immune check point inhibitor selected from: anti-PD1, anti-CTLA4, anti-PDL1 and anti-TIM 3 anti-PD1, anti-CTLA4, anti-PDL1, anti-TIM3, anti-LAG3, anti-IDO, anti-Kir, anti-blta and their combination thereof.

Alternatively, in each of the above embodiments, the BCG can be advantageously replaced by heat killed bacteria selected from: *Mycobacterium tuberculosis* (HKMT), *Salmonella typhimurium* (HKST), *Listeria monocytogenes* (HKLM), *Mycobacterium vaccae*, IMM-101 (*Mycobacterium obuense*) and inactivated *Streptococcus pyogenes* (OK-432/Picibanil) and their combination thereof.

Alternatively, in each of the above embodiments, the BCG can be advantageously replaced by a Lps analogue selected from: MPLA (monophosphoryl lipid A), G100 (glucopranosyl lipid A) and their combination thereof.

Alternatively, in each of the above embodiments, the BCG can be advantageously replaced by a synthetic analogue selected from: Imiquimod, mifamurtide (Synthetic wall analogue of *Mycobacterium tuberculosis*) and their combination thereof.

FIGURE LEGENDS

FIG. 1: Figure showing the micellisation and sol-gel transition as measured by DSC. Differential calorimetry was used to study the influence of the addition of 0.1% w/v xanthan gum Satiaxane® in P407 21% w/v hydrogel and the influence of the addition of the active proteins. Measurements were performed with a DSC SCC7 (Mettler Toledo), with a temperature ranging from $-5°$ C. to $-40°$ C. and a speed of $1°$ C./min. The Temperature of gelification is indicated as Tg or Tgel.

Figure 2:
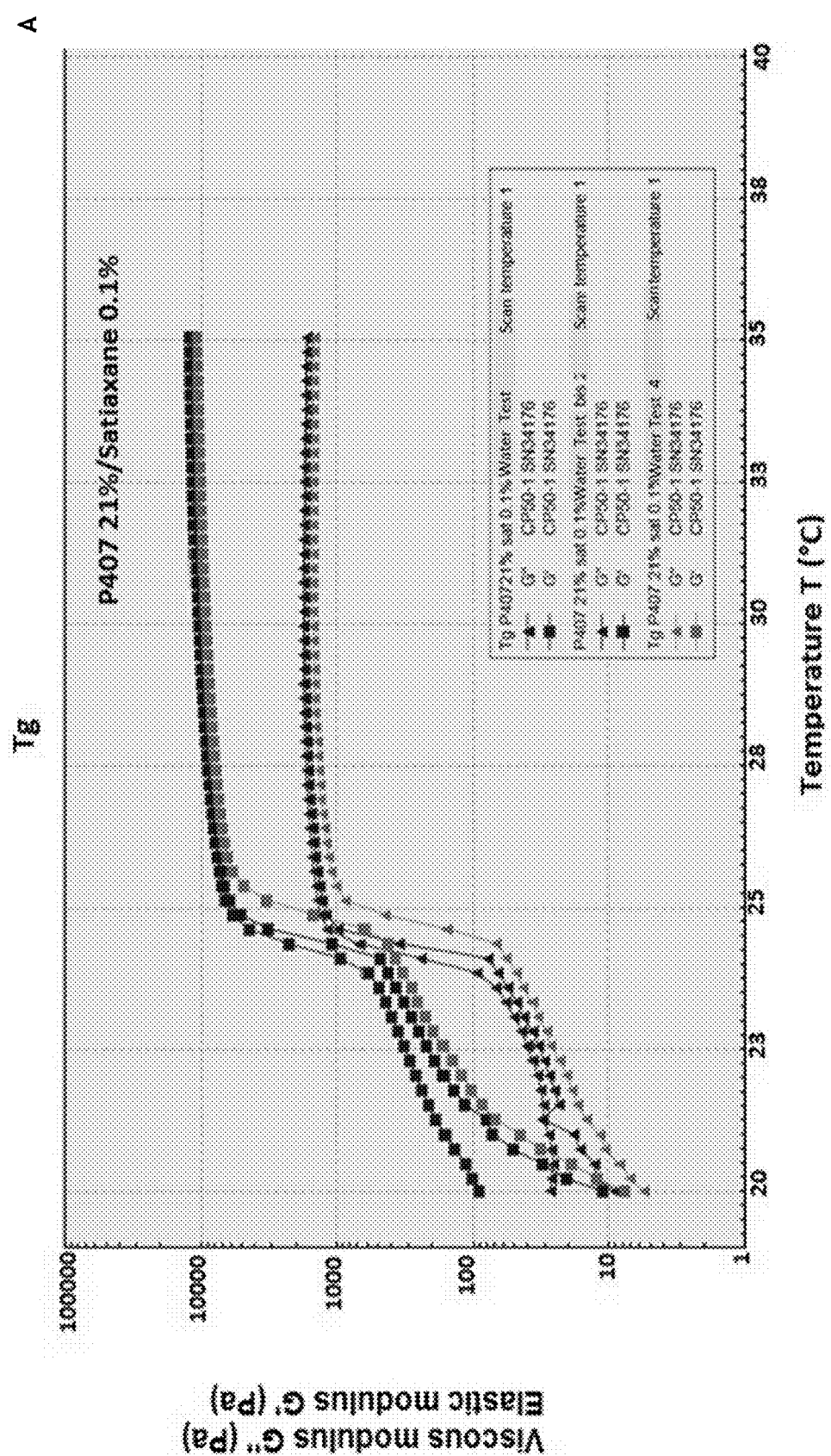
Figure 2:
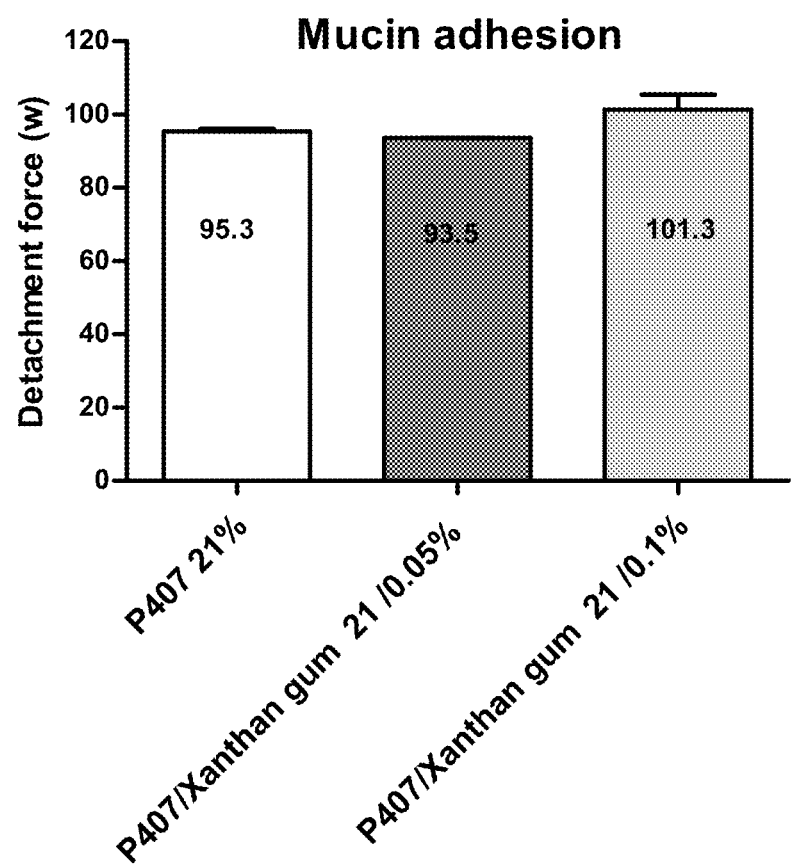

FIG. 2: Figure illustrating the determination of the gel properties by rheology (sol-gel transition in A and gel bioadherence in B).

(A) The gelation temperature of thermosensitive polymerichydrogel P407/Satiaxane® 21/0.1% w/v was determined by rheology using tangent G' and G". (B) The strength required to tear the hydrogel from a mucin scaffold was higher for the P407/Satiaxane® 21/0.1% w/v gel composition than for the P407 21% w/v or P407/Satiaxane® 21/0.05% w/v gel compositions.

Figure 3:
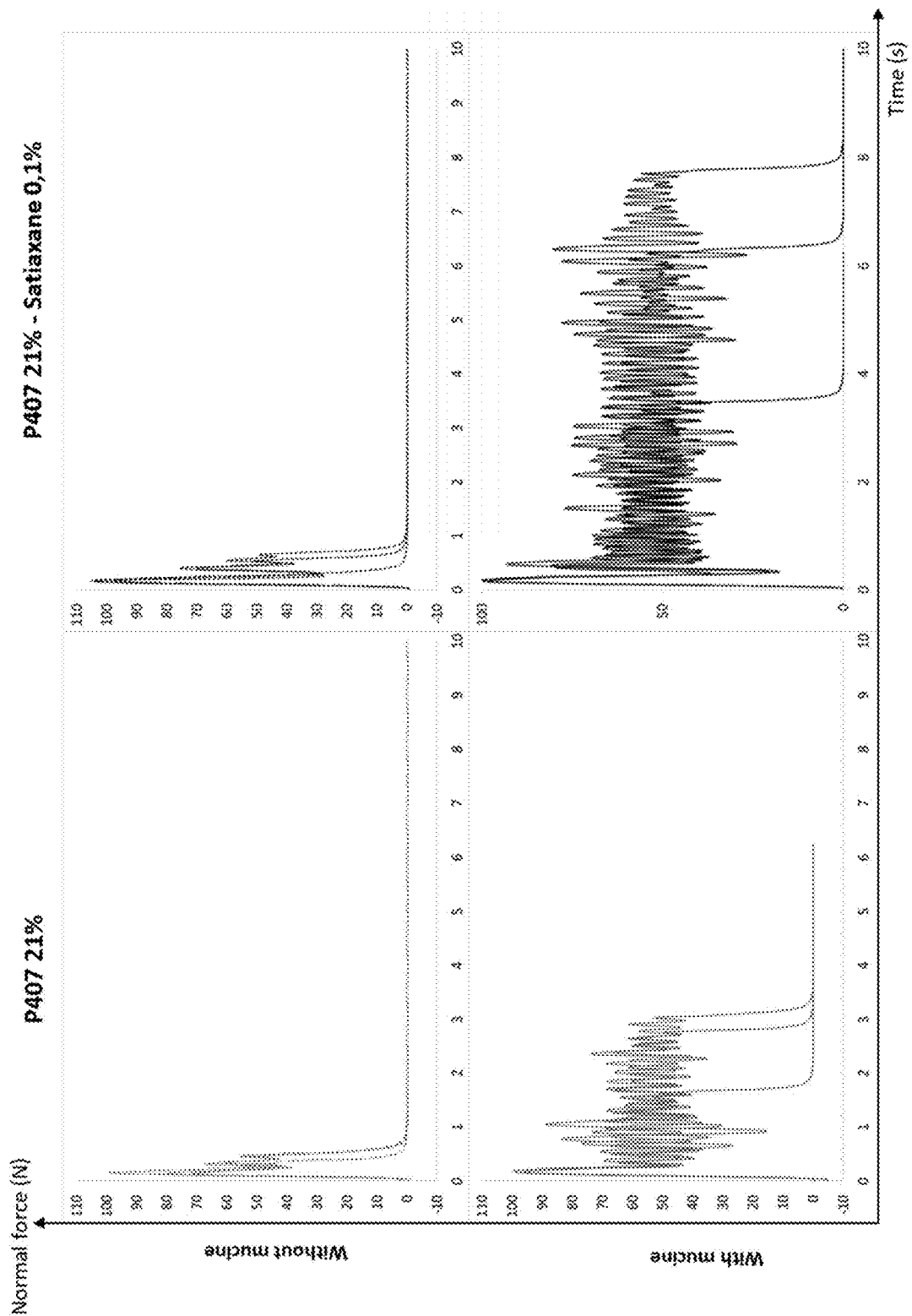

FIG. 3: Figure showing the force and time required to detach the P407 21% w/v and P407/Satiaxane® 21/0.1% w/v sol-gel from a contact surface. The test demonstrates that the force to break the gel is similar (0.5 for P407 alone and 0.6 with satiaxane) when there is no adhesive surface. The presence of mucin at the installation surface shows a time to break equal to 2.7 s for P407 and this time goes up to 6.0 s in presence of Satiaxane®. Satiaxane improves the gel mucoadhesion as compared to P407 alone.

Figure 4:
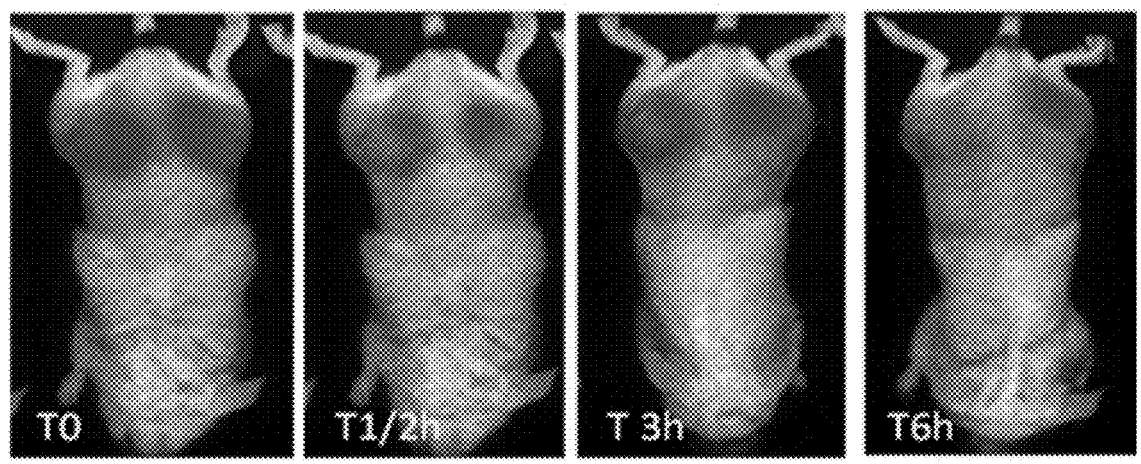
Figure 4:
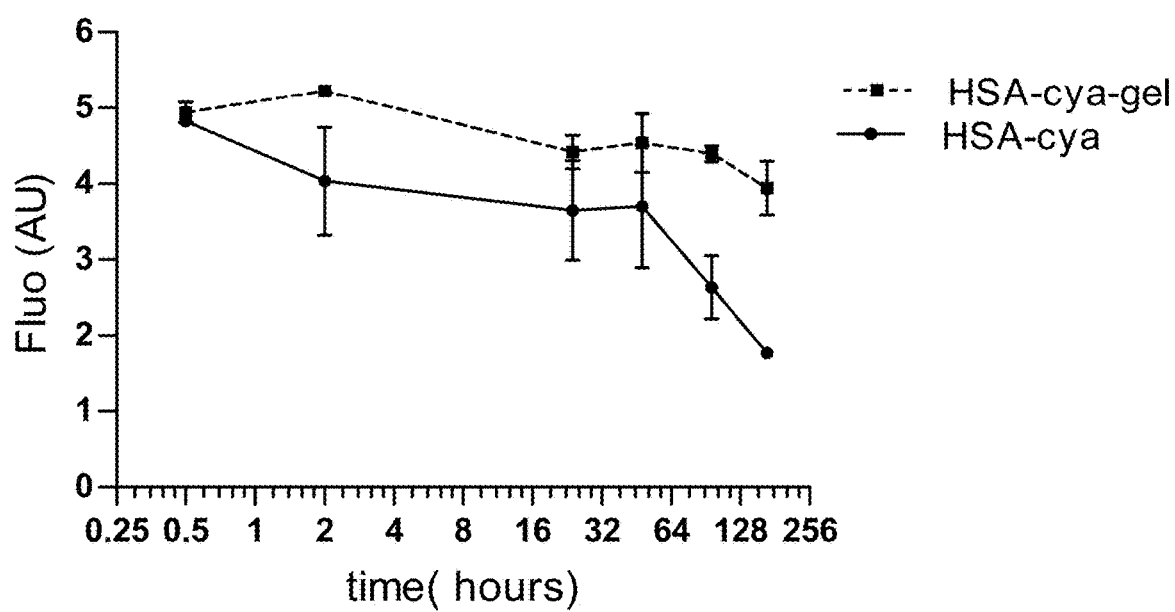

FIG. 4: Figure showing the kinetic of labelled protein release from the thermosensitive hydrogel in vivo.

(A) Longitudinal following of labelled protein release when injected as a thermosensitive polymerichydrogel (left tumor) or as an aqueous solution (right tumor) at 10 days post tumor implantation. (B) The labelled protein was injected intratumorally and fluorescence quantified over time at 0, 0.5, 2, 24, 48, 96 h and 7 days post-injection.

Figure 5:
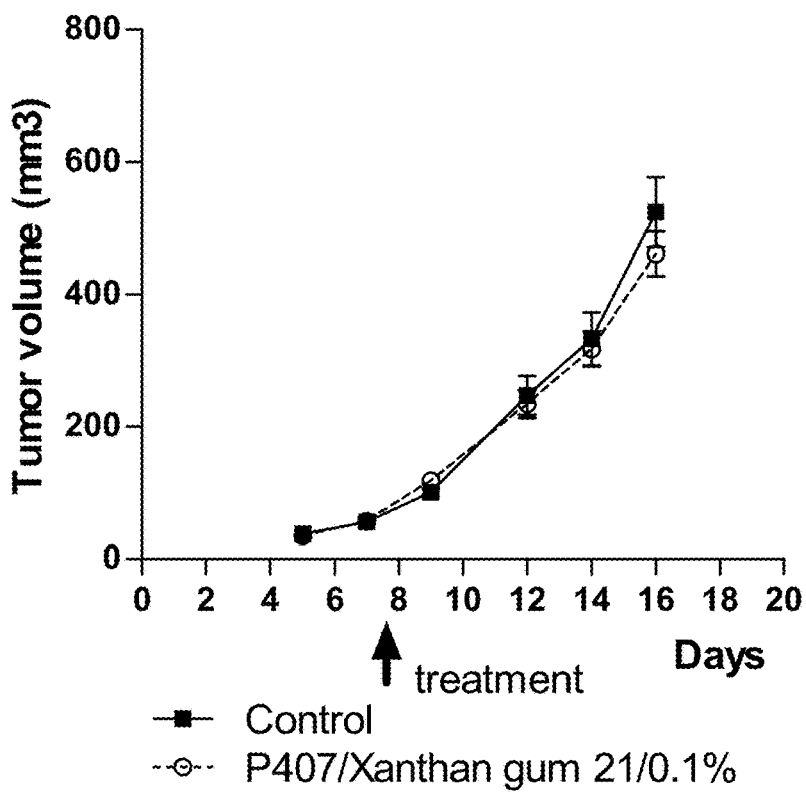
Figure 5:
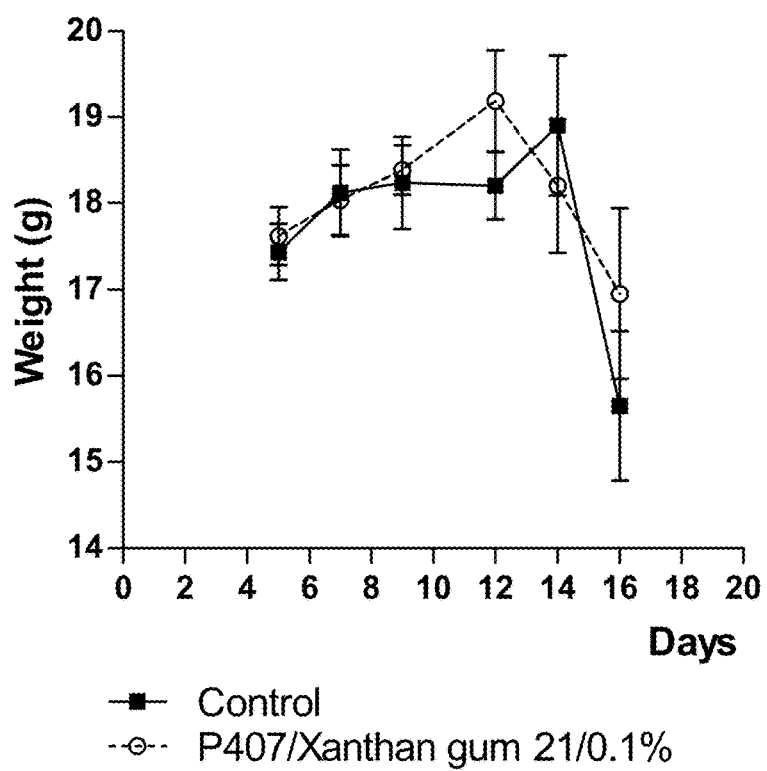

FIG. 5: Graphic representation of the in vivo mice tolerance to the thermosensitive polymeric hydrogel.

A. Follow-up of the tumoral growth for the control group (black line) and the treated group post intratumoral injection of 60 μL of Gel P407/Satiaxane® 21/0.1% w/v (dashed line). B. Follow up of the mice weight for the control group (black line) and the treated group post intratumoral injection of 60 μL of Gel P407/Satiaxane® 21/0.1% w/v (dashed line).

Figure 6:
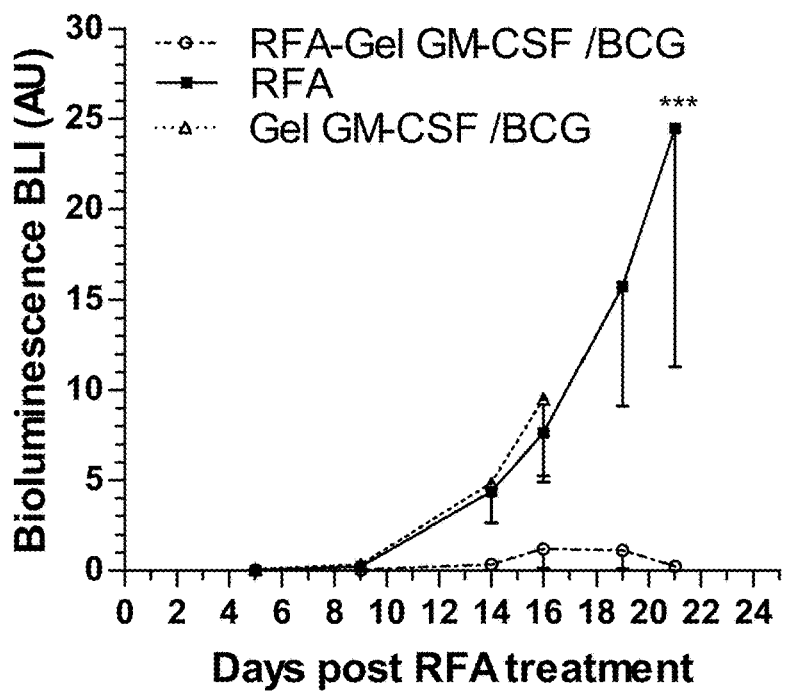
Figure 6:
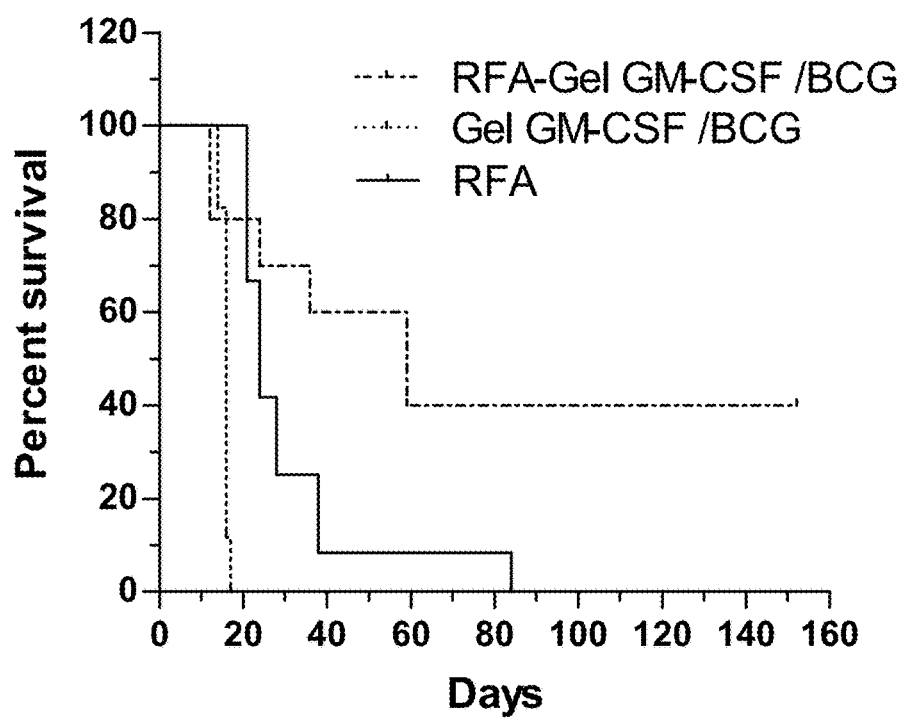

FIG. 6: Graph illustrating the antitumoral efficacy and mice survival using the thermosensitive polymeric hydrogel.

(A) Effect of the treatment on distal tumor growth as measured by bioluminescence. The distal tumors (50,000 cellules/100 μl) were injected subcutaneously on the day of the treatment. The primary tumor was treated with the thermosensitive polymeric hydrogel GM-CSF/BCG alone (triangle, dashed line), radiofrequency ablation (RFA) alone (squares, straight line), or with the association of RFA and the thermosensitive polymeric hydrogel GM-CSF/BCG (empty circles, dashed line). (B) Survival curves of the three groups described in (A), with the percentage of survival expressed as a function of time (days).

Figure 7:
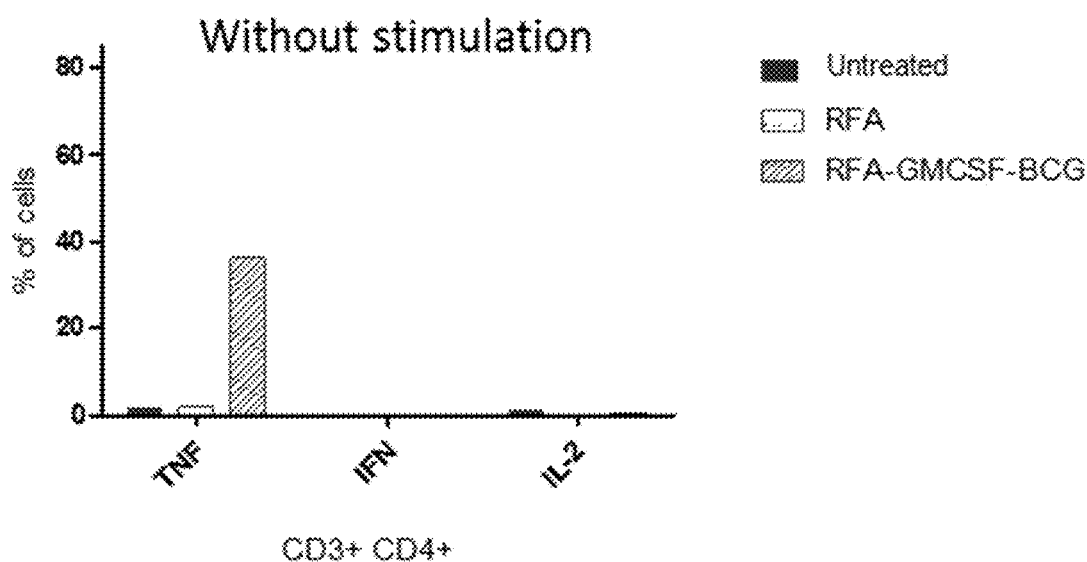
Figure 7:
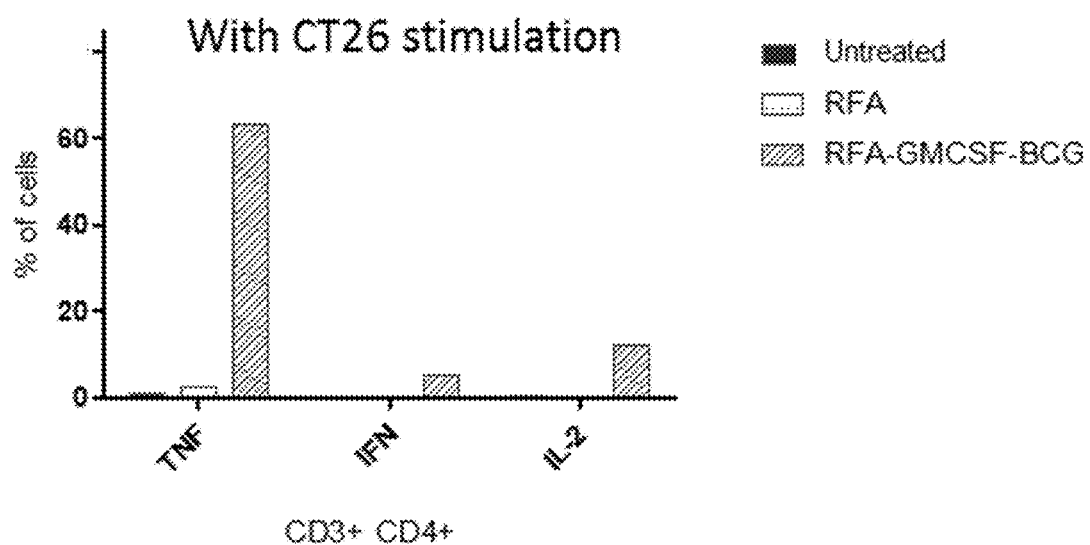
Figure 7:
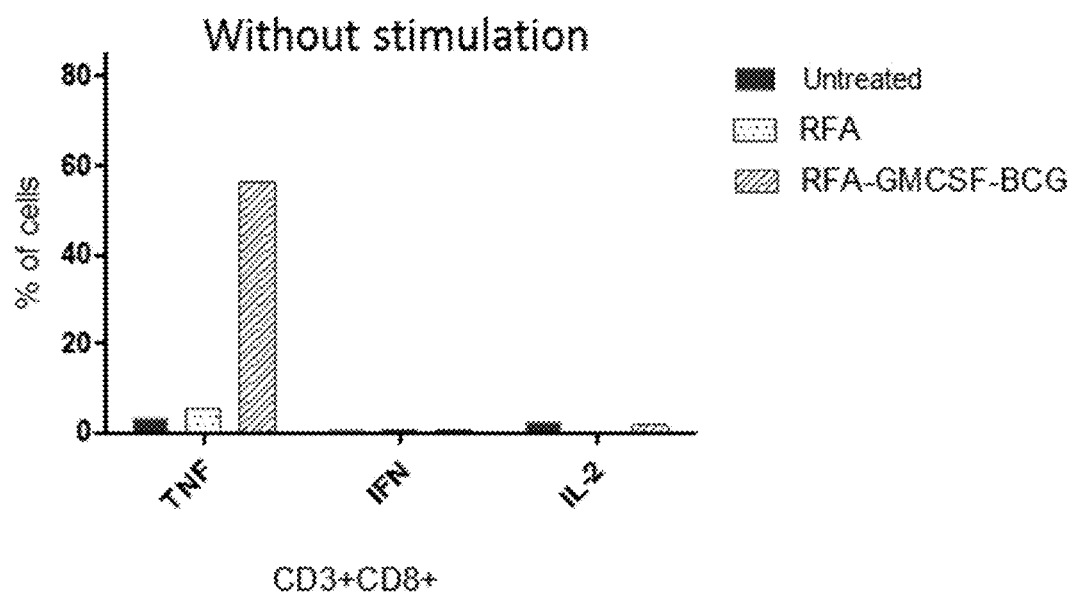
Figure 7:
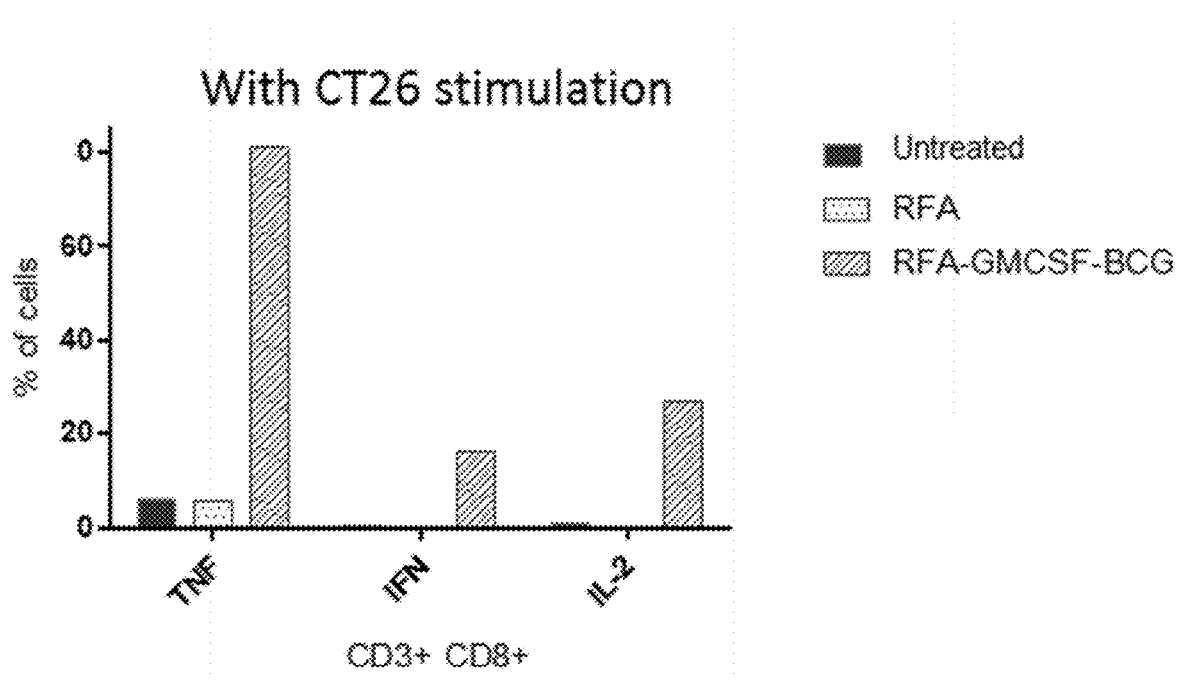

FIG. 7: Graphic representation of the systemic immune response as measured by flow cytometry.

Preliminary results of systemic immunity were measured by flow cytometry. On the day of sacrifice, spleens were collected and the lymphocytes extracted. The production of TNF-α, IFN-γ and IL-2 for the two helper lymphocyte populations CD3+/CD4+ (A and B) and cytotoxic CD3+/CD8+ (C and D) were measured with (B and D) or without (A and C) stimulation in presence of CT26-luc+ cells for the untreated group (n=3), the radiofrequency group (RFA, n=3), and the group treated with the association of radiofrequency and thermosensitive polymeric hydrogel GM-CSF/BCG (RFA-Gel GMCSF-BCG, n=1).

Figure 8:
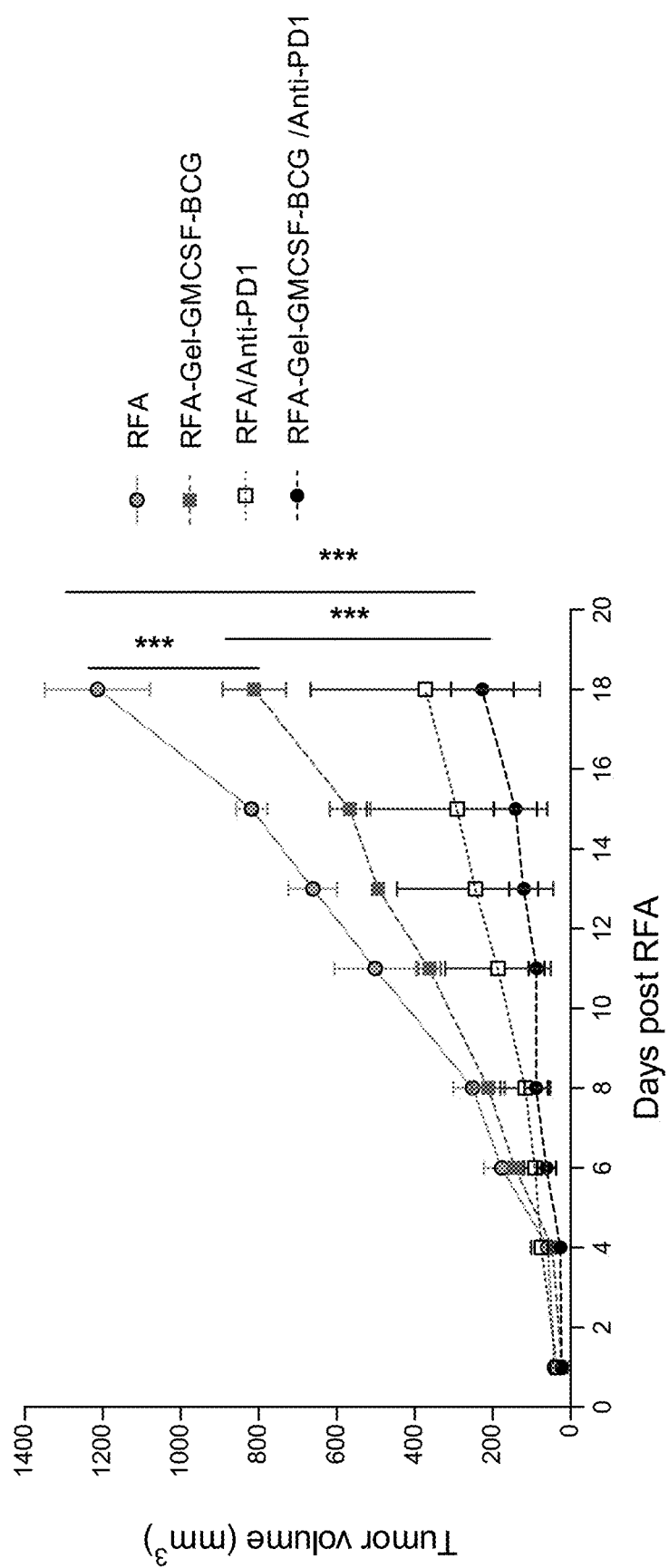

FIG. 8: Graph demonstrating the PD1 therapy response enhanced with RFA-Gel-GMCSF-BCG on macrometastasis.

The ct26-Luc Tumor bearing mice was treated with RFA at day 8, the Gel-GMCSF-BCG was injected locally. PD1 was injected by i.p at day 4, 7, 10, 13 and 16 after RFA. Tumors ("primary" and "secondary") in this model were injected the same day which means that the macro-tumors are distant from the site of RFA at the time of treatment of the tumor I area. The secondary tumor size was measured every 3 days post RFA with calipers (4-6 mice per group). Anova test was performed (values represent means±SEM; ***, P<0.001).

Figure 9:
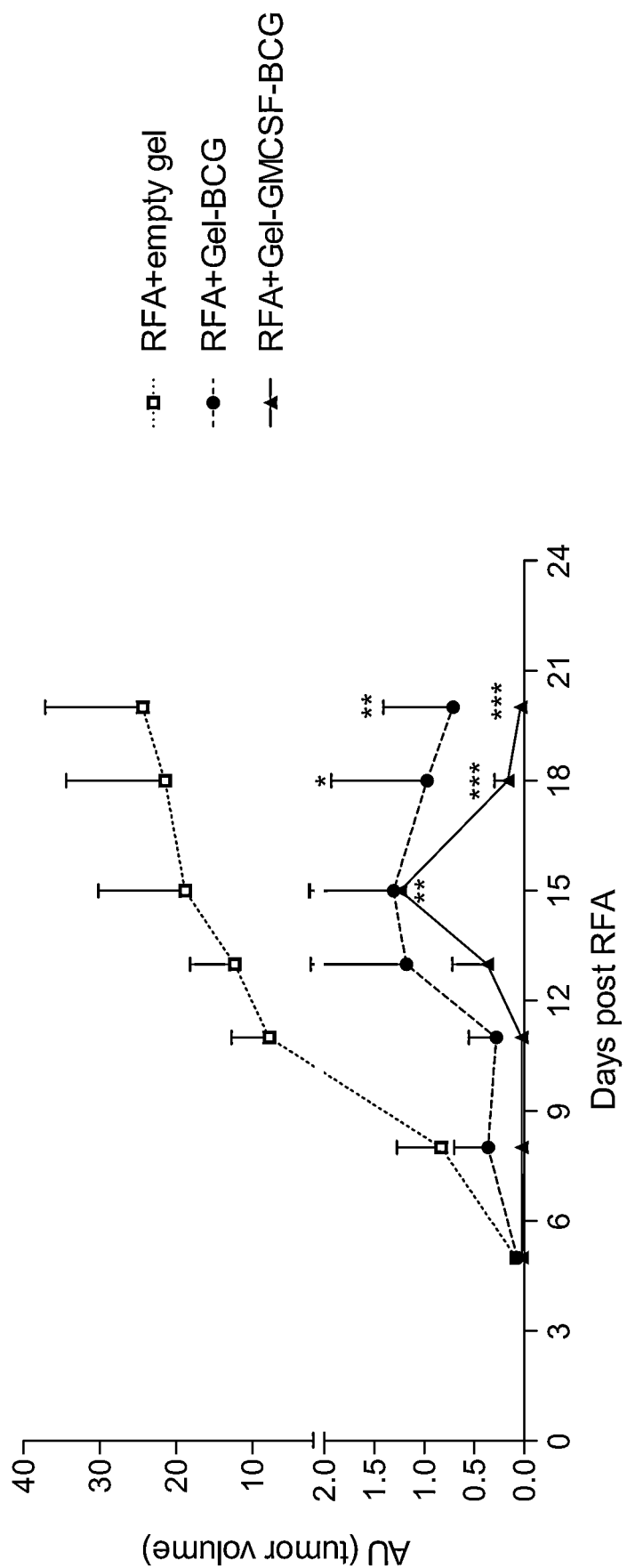

FIG. 9: Graph illustrating the antitumoral efficacy using the thermosensitive polymeric hydrogel GMCSF/BCG on micrometastasis.

Effect of the treatment on distal tumor growth as measured by bioluminescence. The distal tumors (25,000 cellules/100 μl) were injected subcutaneously on the day of the treatment. The primary tumor was treated with (RFA) and empty gel (squares, dashed line), the association of RFA and the thermosensitive polymeric hydrogel-BCG (circles, straight line), or with the association of radiofrequency ablation (RFA) and the thermosensitive polymeric hydrogel GM-CSF/BCG (triangles, dashed line).

Figure 10:
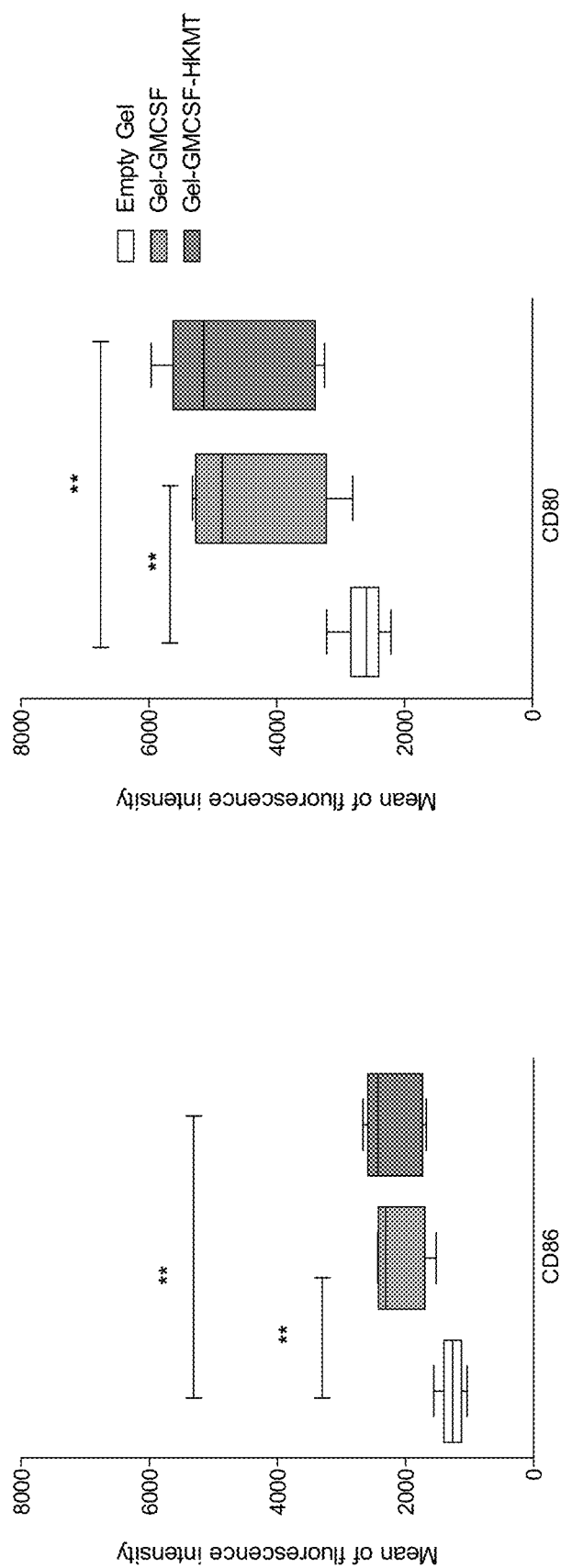

FIG. 10: Figure illustrating the in vitro activation of immature bone marrow dendritic cells with immune gel formulation. The test shows the effect of P407-Satiaxane in dendritic cells activation.

Figure 11:

FIG. 11: Immunohistochemical staining of CD3 lymphocytes in the secondary tumor. Black arrows show CD3 lymphocyte infiltration in secondary tumors. There is a much larger lymphocyte infiltrate around the tumor in RFA+Gel+GMCSF-BCG treated mice compared to mice not receiving treatment

EXAMPLES

Summary

The anti-tumoral efficacy of the Calmette Guerin Bacilla (BCG), widely used in situ in bladder cancer or associated with colorectal-based vaccines, and the GM-CSF, which is able to recruit and mature dendritic cells, has been previously shown in fundamental research as well as in clinical trials. These results motivated the integration of both of these immunomodulators in a thermosensitive polymeric hydrogel to maintain them locally post-local treatment.

Various thermosensitive polymeric hydrogel compositions were evaluated by thermal analyses and rheology to determine gelation temperature and viscosity, and to design a gel able to prolong the release of the active substances. Concentrations of poloxamer 407 (e.g. 40, 26, or 21% w/v), as well as buffers (e.g. water, PBS, or NaCl) were varied. The thermosensitive polymeric hydrogel containing 21% w/v of poloxamer 407 exhibited preferred characteristics in terms of gelation temperature, osmolarity, and viscoelasticity.

In order to stabilize the thermosensitive polymeric hydrogel in the treated tumor, a mucoadhesive gum was added to the formulation. Solutions with various gum concentrations ranging from 0.05 to 0.3% w/v were tested. The thermosensitive polymeric hydrogel P407/Xanthan gum Satiaxane® UCX930 21/0.1% w/v was selected as a preferred formulation for its rheological properties. An example of the results obtained is presented in FIGS. 1 and 2. This formulation was further evaluated in terms of prolonged protein release (FIG. 4), in vivo toxicity (FIG. 5), anti-tumoral efficacy (FIG. 6 and FIG. 9) and lymphocyte recruitment (FIG. 7).

The optimized thermosensitive polymeric hydrogel showed a prolonged protein release of at least 4 days following injection of the labelled protein solution with the thermosensitive polymeric hydrogel, over the labelled protein solution injected alone (FIG. 4). After 16 days, no toxicity was observed within the groups of animals treated. No difference in growth or weight was measured between the control group and the treated group. Our therapeutic strategy was tested on Balb/c mice subcutaneously implanted with CT26 tumors. Mice were vaccinated with BCG 3 weeks prior treatment. A tumor graft was implanted, and then primary tumors were surgically removed using radiofrequency. The thermosensitive polymeric hydrogel was injected locally post resection. On the same day, two secondary tumors were implanted by injection of 25,000 CT26 luciferase positive cells.

Tumor growth was then followed by optical imaging. The results showed statistically significant results between the animals treated with RFA alone (n=11), thermosensitive polymeric hydrogel alone (n=6) or the complete treatment consisting of RFA resection followed by thermosensitive polymeric hydrogel injection (n=10) (FIG. 6). Survival was significantly improved. The mean survival was 14 days for mice treated with the hydrogel alone, 39 days for mice treated with RFA alone and 152 days for the RFA+thermosensitive hydroGel complete treatment. Lymphocyte quantification within the spleen of treated animals showed that the complete treatment induced lymphocyte recruitment, as expected (FIG. 7).

Example 1: Thermosensitive Polymeric Hydrogel Preparation

The xanthan gum Satiaxane® UCX930 (0.05% w/v, 0.1% w/v, 0.2% w/v, 0.3% w/v) was dissolved in ⅔ of the final volume in deionized water with agitation for 1 h at room temperature. Poloxamer 407 was added to the solution and incubated overnight at 4° C. The mixture was then completed to the final volume with deionized water. Solutions are maintained at 4° C. and can be filter sterilized.

Example 2: Measurement of the Sol-Gel Transition Using DSC

The sample (20 mg) is introduced in an aluminum pan (40 µL) with a cover (ME26763). The crucible is crimped with a press (ME 51140547) and then placed in the oven of the system with an empty crucible as a reference. The analysis is performed at a speed of 5° C./min and a temperature ramp of −5 to −40° C. using a DSC1 (Mettler Toledo) equipped with a HSS7 sensor and an intracooler (Hueber, −40° C.)(FIG. 1). The first endothermic peak corresponds to the micellisation transition allowing the determination of the critical micellar temperature (CMT). The second transition of weaker energy corresponds to the gelation transition allowing the determination of gelation temperature taken at the maximal signal.

Example 3: Measurement of the Sol-Gel Transition Using Rheology

The rheometer (MC102) is warmed up and the system calibrated with the mobile CP50-1. A volume of 750 µl is loaded on the support then the mobile goes down at a distance equal to 0.1 mm from the support. A first test (Amplitude sweep) defines the linearity of the two modules G' (storage modulus) and G" (loss modulus) submitted to a shearing force Y (FIG. 2). A temperature increase is then performed in triplicate at a speed of 1° C./min and a ramp from 20° C. to 40° C. The gelation temperature was determined by the tangent of the curve G'.

Example 4: Measurement of Gel Bioadherence Using Rheology

The system is placed in a mucin bath (Mucin from porcine stomach Type II, Sigma Aldrich) and incubated at 37° C. for 10 minutes. When the film is dried, the mobile is settled and the sample loaded on the support of the apparatus. The mobile is brought down to a distance of 0.1 mm from the support. The strength required to tear the gel is measured at 37° C. (Detachment Force).

The thermosensitive polymeric hydrogel P407/Xanthan gum Satiaxane® UCX930 21/0.1% w/v was selected as the preferred formulation based on Examples 2 to 4 (see FIGS. 1 and 2). Further analyses were performed with this formulation.

Example 5

Measurement of gelification temperature (Tg) of hydrogel formulations comprising various poloxamer and mucoadhesive agents. Each formulation was analyzed three times (table 1 present mean±S.D). All gels tested show a range of Tgel between 21 and 28° C. ND: not determined.

TABLE 1

Gelification temperature of various hydrogel formulations

| Hydrogel formulation | Tg (° C.) |
|---|---|
| P407 20% - P188 2% | 26.5 ± 0.1 |
| P407 20% - P188 2% - chitosan 0.25% | 27.7 ± 0.05 |
| P407 20% - P188 2% - chitosan 0.5% | 27.1 ± 0.05 |
| P407 20% - P188 2% - chitosan 1% | 26.5 ± 0.2 |
| P407 20% - P188 2% - protanal 0.25% | 27.0 ± 0.2 |
| P407 20% - P188 2% - protanal 0.5% | 26.0 ± 0.1 |
| P407 20% - P188 2% - protanal 1% | 25.4 ± 0.1 |
| P407 20% - P188 2% - satiaxane 0.05% | 26.6 ± 0.3 |
| P407 20% - P188 2% - satiaxane 0.1% | 27.9 ± 0.1 |
| P407 21% | 21.4 ± 0.1 |
| P407 21% - satiaxane 0.05% | 22.1 ± 0.8 |
| P407 21% - satiaxane 0.1% | 21.9 ± 0.8 |
| P407 21% - satiaxane 0.2% | ND |

Example 6. In Vitro Mucoadhesion Test

Adhesion test was carried out using an Anton Paar rheometer, model MCR 102, fitted with a 50 mm plane-plane mobile geometry. Two formulations of sol-gel were tested: P407 21% w/v and P407/satiaxane 21/0.1% w/v. Porcine gastric mucin of type II (MUC2) was used as received without further purification.

The test consists of measuring the required normal force and time to detach the sol-gel from a contact surface. Two conditions were performed by loading sol-gel samples on the Peltier plate. First condition consisted of moving the mobile geometry towards the sample, after a contact time with the latter, the mobile moves in the opposite direction at a precise speed (5000 µm/sec), causing the gel to elongate and then to detach from the mobile. Second condition consisted of depositing a layer of mucin dispersion (5% w/v) on the mobile geometry prior to measurement.

Adhesion test was conducted at 37° C. to mimic physiological temperature. A solvent trap covering the geometry was used to prevent evaporation, because sample dehydration would seriously affect the rheological properties of the sample.

Both conditions were performed and normal force and time required to detach the sol-gel were recorded over time. The higher the normal force and the longer the time, the stronger is the adhesion.

The test demonstrates the effect of satiaxane on gel adhesion (FIG. 3). We observe that the force to break the gel is similar 0.5 for P407 alone and 0.6 with satiaxane when there is no adhesive surface. The presence of mucin at the installation surface, shows a time to break equal to 2.7 s for P407 and this time goes up to 6.0 s in presence of satiaxane. Satiaxane improves the gel mucoadhesion as compared to P407 alone.

Example 7: Kinetics of Labelled Protein Release from the Thermosensitive Polymeric Hydrogel In Vivo CT26 tumors are induced by subcutaneous implantation of a tumor fragment (30 mm$^3$) on both mouse flanks (FIG. 4). At day 10 post-implantation, mice were anesthetized with an i.p injection of a Xylazine (10 mg/kg)/Ketamine (80 mg/kg) mixture. After shaving, intratumoral injections were performed. In the left tumor, labelled protein embedded in the thermosensitive polymeric hydrogel P407 21% w/v/xantham gum Satiaxane® 0.1% w/v/HSA-Cyanin (60 µl, 0.5 mg/ml H$_2$O) was injected. In the right tumor, an aqueous solution of HSA-Cyanin protein (60 µl, 0.5 mg/ml H$_2$O) was injected. At t0 post-injection, an optical image is taken. Additional images are taken during 5 seconds at the following time points 0.5 h; 2 h, 24 h, 48 h, 96 h and 7 days post-injection. Fluorescent signal quantification was performed over a region of interest (ROI) applied to the tumors using the M3 vision software (Biospace Lab). Results are expressed with the formula: Fluo (AU)=fluorescence value at tx/fluorescence value at t 0.

The optimized thermosensitive polymeric hydrogel showed a prolonged protein release of at least 4 days following injection when compared to the aqueous solution of labeled protein (see FIG. 4).

Example 8: Tolerance to the Thermosensitive Polymeric Hydrogels In Vivo

A subcutaneous implantation of CT26-Luc fragments (30 mm$^3$) was performed on both flanks of Balb/c mice. The gel P407 21% w/v/xanthan gum Satiaxane® 0.1% w/v (60 µl) was injected 8 days after tumor implantation. Longitudinal tumor growth was measured with a caliper and the weight of the mice was noted as function of time for 16 days. An ANOVA test was performed for statistical comparison. The classical follow up of the behavior, hair change and weight loss were also performed every day.

After 16 days, no toxicity was observed within the groups of animals treated. No difference in growth or weight was measured between the control group and the treated group (see FIG. 5).

Example 9: Efficacy of Local Immune Stimulation by Proteins Inserted within a Thermosensitive Polymeric Hydrogel 9.1. Tumor Volume Follow-Up for Primary and Secondary Micrometastasis Tumors Balb/c JRJ (6-8 weeks) mice were vaccinated by subcutaneous injection of 5×10$^6$ CFU of BCG (Sanofi Pasteur). Three weeks later, a CT26-Luc fragment (30 mm$^3$) was implanted on the mice flanks. Mice were anesthetized with an i.p injection of a Xylazine (10 mg/kg)/Ketamine (80 mg/kg) mixture 8 days post-implantation.

Radiofrequency was applied with the RF generator CC-1 Cosman Coagulation System (Radionics, Burlington, Mass., USA). A small incision was performed in order to isolate the primary tumor. A radiofrequency probe (Cool-Tip™ RFA Single Electrode Kit, 15-1 cm Covidien™, Medtronic) was introduced within the primary tumor. Parameters such as impedance, time and temperature were noted (power 2-4 volts, electrical impedance: 300-700 amperes). The probe was removed when the temperature reached 60° C. within the tumor. The skin is stitched and 60 µl of P407 21% w/v/Xanthan gum Satiaxane® 0.1% w/v hydrogel containing or not GMCSF (5 µg)+BCG (5×10$^6$ CFU) was injected intratumorally. At the same time, secondary tumors were induced by subcutaneous injection of 25000 CT26-Luc cells on both mouse sides. Primary and secondary (distal) tumor growth was followed by bioluminescent imaging every 3 days. For this, an i.p injection of luciferin (2 mg) was performed and the bioluminescent signal was acquired with PhotonIMAGER™ OPTIMA CCDi Camera (objective 50 mm) for 10 minutes, 20 minutes after the injection of the luciferin. The survival curve is determined with 1000 mm$^3$ as the tumor growth limit. When the distal tumors reached this volume, mice were sacrificed. Spleen and distal tumors were removed in order to analyze the immune response by flow cytometry and immunohistochemistry.

The results showed statistically significant results between the animals treated with RFA alone (n=11), thermosensitive polymeric hydrogel alone (n=6) or the complete treatment consisting of RFA resection followed by thermosensitive polymeric hydrogel injection (n=10) (see FIG. 6A and FIG. 9). Survival was significantly improved (see FIG. 6B). Mean survival was 14 days for mice treated with the hydrogel alone, 39 days for mice treated with RFA alone and 152 days for the RFA+Gel complete treatment (FIG. 6A).

9.2. Analysis of the Systemic Immune Response by Flow Cytometry.

Twenty-two days after RFA treatment, mice were sacrificed and spleens removed under sterile conditions. Speens were dissociated with a potter in cell culture medium (RPMI 1640 1×+glutamax, Gibco, 10% w/v foetal bovine serum FBS, 1% w/v Penicillin-Streptomycin). The cell solution was filtered (cell strainer 70 µm), and centrifuged 400-500×g for 5 minutes. The cell pellet is incubated with a lysis buffer (3 ml, BD PharmLyse™ Buffer 555899) for 5 min at room temperature. The isolated cells were counted and transferred to a 6-well culture plate at a concentration of 100,000 cells/well. In stimulation conditions, this plate was previously prepared with CT26luc+ cells (20,000 cells/well) incubated overnight (5% w/v $CO_2$, 37° C.) and heated to 46° C. for 1 hour to mimic radiofrequency. After overnight incubation, splenocytes were stained with anti-CD3 (PE-Cy 7 Rat Anti-Mouse, BD Bioscience), anti-CD4 (APC Rat Anti-Mouse, BD Bioscience), anti-CD8 (APC-Cy 7 Rat Anti-Mouse, BD Bioscience) and anti-NK (BV421 Rat Anti-Mouse CD49b, BD bioscience) antibodies. Cells were washed and treated with a fixation permeabilization kit (554722 BD bioscience). Intracellular cytokines were detected with IFN-γ (Alexa Fluor® 488 Rat Anti-Mouse IFN-γ), TNF-α (FITC Rat Anti-Mouse TNF) and IL-2 (Alexa Fluor® 488 Rat Anti-Mouse IL-2) antibodies. Data acquisition and analysis of samples was performed using a flow cytometer (BD FacsCanto III).

Lymphocyte quantification showed that the complete treatment induced lymphocyte recruitment (see FIG. 7).

Example 10: Immune Escape of Large Secondary Lesions was Reversed by Association of RFA-Immunogel Vaccination with Systemic Checkpoint Inhibition, Separately Less Effective 10.1 Tumor Cells The CT26 colon adenocarcinoma was obtained from ATCC. The CT26 cell line was purchased from American Type Culture Collection (ATCC, CRL-2638, LGC Standards, Molsheim, France). The CT26-Luc cell line was generated by transfection of the parental CT26 cell line with the luciferase gene as reporter and cultured at 37° C. in a 5% w/v $CO_2$-humidified atmosphere in Dulbecco's Modified Eagle Medium containing 10% w/v fetal bovine serum, 100 µM of streptomycin, 100 U/mL of penicillin and 4 mg/ml of Geneticin. Tumors ("primary" and "secondary") in this model were injected the same day which means that the macro-tumors are distant from the site of RFA at the time of treatment of the tumor I area.

10.2 Tumor Model and RFA Procedure

The mice were vaccinated by subcutaneous injection of BCG ($5*10^5$ CFU/50 µl). Three weeks later, a mouse bearing subcutaneous CT26-Luc tumour was sacrificed, the tumour was resected, placed into sterile Phosphate buffer, cut into fragments of 30 $mm^3$ and inserted subcutaneously using a 12 gauge trocar (38 mm) into the two mouse flanks previously disinfected with alcohol.

Treatments were initiated when the tumor volume reached about 500 mm3. Indeed, animals were anesthetized by i.p injection of Ketamin (80 mg/ml) and Xylazin (10 mg/ml). The ablation was performed using a radiofrequency probe inserted into the center of the right tumor. The probe was removed when temperature reached 60° C. within the tumor to ensure complete ablation of target tumors.

10.3 Hydrogel Injection

The hydrogel P407 21% w/v/Satiaxane 0.1% w/v was prepared as previously described (Data not shown). Five minutes after RFA, 60 µl of hydrogel P407 21% w/v/Satiaxane 0.1% w/v containing 5 µg of recombinant GM-CSF and $5*10^5$ CFU of BCG were injected in the right tumor using a 23 gauge needle. Anti-PD1 therapy was then performed by administering 200 µg of anti-PD-1 through i.p. injection to mice every 3 days for a total of five times. Tumors were measured with a digital caliper every 3 days. Tumor volumes were calculated in cubic millimeter using the following formula: length×(width)$^2$]/2. Data shown are mean tumor volume+/−SE. Data analysis was performed using Graph Pad (Prism5).

The results showed that the association of RFA, the thermogel and the anti-PD1 presents a higher antitumoral efficacy than the use of the RFA and the anti-pd1 alone (see FIG. 8).

Example 11. In Vitro Activation of Immature Bone Marrow Dendritic Cells with Immune Gel Formulation Immature Dendritic Cells were generated from bone marrow (BMDCs) of healthy mouse. $10^7$ bone marrow cells were cultured in appropriate medium with addition of GM-CSF (20 ng/ml) at 37° C., 5% $CO_2$. At day 6, immature dendritic cells are discovered and the activation test is performed. To test the activation of BMDCs, 24 wells plates with transwell inserts were used. Various gels (empty gel, gel with GM-CSF and gel with GM-CSF and HKMT) were placed in wells (6 wells/gel). After gelification, the medium was added and a transwell inserted. Then, BMDCs in appropriate medium were added in the insert. Plates were incubated for 24 hours. The BMDCs which have crossed over transwell membranes were labeled with CD80 and CD86 and counted using flow cytometry. The test shows the effect of P407-Satiaxane in dendritic cells activation. We observe that the Empty gel shows a few activation level (see FIG. 10). Gel with GM-CSF with or without HKMT shows higher activation than empty gel (significant differences). There is no difference between gel with GM-CSF and gel with GM-CSF and HKMT.

In conclusion, the gel allows the diffusion of GM-CSF and HKMT and maintain the activation faculties of the dendritic cell thanks to the release of these molecules.

Example 12. Immunohistochemical Staining of CD3 Lymphocytes in the Secondary Tumor At day 17 after treatment, tumors were harvested, fixed and embedded in paraffin. Tissue were cut and put down on slides (Superfrost Plus) and stained with Rabbit anti human purified CD3 at 4° C. Endogenous peroxidase activity was quenched with H2O2, subsequently, slides were incubated with secondary antibody rabbit N-Histofine during 30 min at room temperature and DAB-chromogen. Tissue sections were counterstained with Gill's hematoxylin. Slides were analyzed using mirax slides scanner.

Black arrows demonstrate CD3 lymphocyte infiltration in secondary tumors (see FIG. 11). There is a much larger lymphocyte infiltrate around the tumor in RFA+Gel+GMCSF-BCG treated mice compared to mice not receiving treatment.

REFERENCES

Allard et al., 2012, *Diagn Pathol.* 7:156.
Baggiolini, 1998, *Nature.* 392:565-568.
den Brok et al., 2004, *Cancer Res.* 64(11):4024-9.
Driessens et al., 2011, *Cancer Immunol Immunother.* 60(2): 273-81.
Guo et al., 2014, *Nan Fang Yi Ke Da Xue Xue Bao.* 34(5):674-8.
Hansler et al., 2006, *World J Gastroenterol.* 12(23):3716-21.
Hompes et al., 2011, *Cancer Imaging.* 11:23-30.
Liu et al., 2009, *Mol Ther.* 17(12):2049-57.
Malafosse et al., 2001, *Ann Oncol.* 12(7):887-94.
Mosolits et al. 2005, *Expert Rev Vaccines.* 4(3):329-50.
Nakamoto et al., 2007, *Clin Exp Immunol.* 147(2):296-305.
Nemunaitis, 2005, *Expert Rev Vaccines.* 4(3):259-74.
Nordlinger et al., 2013, *Lancet Oncol.* 14(12):1208-15.
Nordlinger et al., 2003, *Colorectal Dis.* 5(5):515-7.
Rollins, 1997, *Blood.* 90(3):909-92.
Ruers et al., 2012, *Ann Oncol.* 23(10):2619-26.
Su et al., 2016, *Clin Lab.* 62(4):599-608.

The invention claimed is:

1. A thermosensitive mucoadhesive polymeric hydrogel comprising:
   at least one thermosensitive copolymer, consisting of poloxamer 407 at a concentration of 21% w/v, in one aqueous solution; and
   xantham gum at a concentration of 0.1% w/v;
wherein said thermosensitive polymeric hydrogel further comprises at least one immunostimulatory adjuvant and at least one cytokine and/or at least one chemokine and/or at least one heat shock protein, and wherein said hydrogel presents a gelification temperature between 21° C. and 28° C., and can be administered as a flowable liquid but will gelify on the tissue of interest.

2. A method for the treatment of tumors or metastasis in a subject having a cancer, comprising the administration of a thermosensitive mucoadhesive polymeric hydrogel to said subject, wherein said hydrogel comprises:
   at least one thermosensitive copolymer consisting of poloxamer 407, at a concentration of 21% w/v, in one aqueous solution; and
   xantham gum at a concentration of 0.1% w/v;
wherein said thermosensitive polymeric hydrogel further comprises at least one immunostimulatory adjuvant and at least one cytokine and/or at least one chemokine and/or at least one heat shock protein, and wherein said hydrogel presents a gelification temperature between 21° C. and 28° C., and can be administered as a flowable liquid but will gelify on the tissue of interest.

3. A thermosensitive mucoadhesive polymeric hydrogel according to claim 1, wherein said thermosensitive polymeric hydrogel allows controlling release of said immunostimulatory adjuvant and said cytokine and/or said chemokine and/or said heat shock protein, under physiological conditions, over a period from at least 12 hours to 12 days.

4. A method for the treatment of tumors or metastasis according to claim 2, wherein said cancer is selected from colorectal cancer, hepatocellular carcinoma, melanoma, kidney cancer, lung cancer, breast cancer, pancreatic cancer, and bone cancer.

5. A thermosensitive mucoadhesive polymeric hydrogel according to claim 1, wherein said immunostimulatory adjuvant is selected from the group consisting of:
   *Bacillus* Calmette-Guérin (BCG) and/or at least one of its purified proteins;
   (ii) CpG oligodeoxynucleotides (CpG ODN), or any attenuated bacterial or viral agents and derivatives thereof having a specific or a non-specific anti-tumoral activity;
   (iii) a heat killed bacteria selected from: *Mycobacterium tuberculosis* (HKMT), *Salmonella typhimurium* (HKST), *Listeria monocytogenes* (HKLM), *Mycobacterium* vaccae, *Mycobacterium obuense* and inactivated *Streptococcus pyogenes* and combinations thereof, or
   (iv) an Lps analog selected from: MPLA (monophosphoryl lipid A), G100 (glucopranosyl lipid A), and combinations thereof; and
   (v) a synthetic analog selected from: Imiquimod, mifamurtide, and combinations thereof.

6. A thermosensitive mucoadhesive polymeric hydrogel according to claim 1, wherein said cytokine and/or said chemokine and/or said heat shock protein are selected from the group consisting of: granulocyte macrophage colony stimulating factor (GMCSF), granulocyte colony stimulating factor (GCSF), IL 12, Interferon γ, TNF α, GP96, heat shock protein (HSP), and HSP70.

7. A method for the treatment of cancer tumors or metastasis according to claim 2, wherein said thermosensitive mucoadhesive polymeric hydrogel is used along with:
   (i) a thermal locoregional treatment, or
   (ii) cryotherapy, or
   (iii) embolization, and/or
   (iv) an anti-tumoral treatment,
and wherein said thermosensitive polymeric hydrogel is administered concomitantly or sequentially.

8. A method for the treatment of cancer tumors or metastasis according to claim 2, wherein said thermosensitive polymeric hydrogel is administered concomitantly with a Radio Frequency Ablation (RFA) and sequentially with a systemic immune check point inhibitor that is selected from the group consisting of: anti-PD1, anti-CTLA4, anti-PDL1, anti-TIM3, anti-LAG3, anti-IDO, anti-Kir, anti-blta, and combinations thereof.

9. A kit comprising:
   (i) a thermosensitive mucoadhesive polymeric hydrogel comprising:
      at least one thermosensitive copolymer consisting of poloxamer 407 in a concentration of 21% w/v, in one aqueous solution; and
      xantham gum in a concentration of 0.1% w/v,
      wherein said hydrogel presents a gelification temperature between 21° C. and 28° C., and can be administered as a flowable liquid but will gelify on the tissue of interest;
   (ii) at least one immunostimulatory adjuvant selected from the group consisting of:
      *Bacillus* Calmette Guerin BCG and/or at least one of its purified proteins;
      CpG oligodeoxynucleotides (CpG ODN);
      attenuated bacterial, viral agents and derivatives thereof having a specific or a non-specific anti-tumoral activity;
      heat killed bacteria selected from: *Mycobacterium tuberculosis* (HKMT), *Salmonella typhimurium*

(HKST), *Listeria monocytogenes* (HKLM), *Mycobacterium* vaccae, *Mycobacterium obuense* and inactivated *Streptococcus pyogenes*, and combinations thereof; or
an Lps analog selected from: MPLA (monophosphoryl lipid A), G100 (glucopranosyl lipid A) and combinations thereof; and
synthetic analog selected from the group consisting of: Imiquimod, mifamurtide, and combinations thereof;
(iii) at least one cytokine and/or at least one chemokine and/or at least one heat shock protein selected from the group consisting of: granulocyte macrophage colony stimulating factor (GMCSF), granulocyte colony stimulating factor (GCSF), IL12, Interferon γ, TNFα, GP96, heat shock protein (HSP), and HSP70.

10. A method of treatment according to claim 2, wherein said thermosensitive mucoadhesive polymeric hydrogel allows controlling release of said immunostimulatory adjuvant and/or said cytokine and/or said chemokine and/or said heat shock protein, under physiological conditions, over a period from at least 12 hours to 12 days.

11. A method of treatment according to claim 2, wherein said immunostimulatory adjuvant is selected from the group consisting of:
*Bacillus* Calmette-Guérin BCG and/or at least one of its purified proteins;
(ii) CpG oligodeoxynucleotides (CpG ODN), or any attenuated bacterial or viral agents and derivatives thereof having a specific or a non-specific anti-tumoral activity;
(iii) a heat killed bacteria selected from: *Mycobacterium tuberculosis* (HKMT), *Salmonella typhimurium* (HKST), *Listeria monocytogenes* (HKLM), *Mycobacterium* vaccae, *Mycobacterium obuense* and inactivated *Streptococcus pyogenes*, and combinations thereof, or
(iv) an Lps analog selected from: MPLA (monophosphoryl lipid A), G100 (glucopranosyl lipid A) and combinations thereof; and
(v) a synthetic analog selected from: Imiquimod, mifamurtide, and combinations thereof.

12. A method of treatment according to claim 2, wherein said cytokine and/or said chemokine and/or said heat shock protein are selected from the group consisting of: granulocyte macrophage colony stimulating factor (GMCSF), granulocyte colony stimulating factor (GCSF), IL 12, Interferon γ, TNF α, GP96, heat shock protein (HSP), and HSP70.

13. A thermosensitive mucoadhesive polymeric hydrogel according to claim 1, wherein the sol-gel transition of the thermosensitive copolymer is reversible in the hydrogel.

* * * * *